US009994616B2

(12) United States Patent
Suga et al.

(10) Patent No.: US 9,994,616 B2
(45) Date of Patent: Jun. 12, 2018

(54) C-MET PROTEIN AGONIST

(71) Applicant: The University of Tokyo, Tokyo (JP)

(72) Inventors: Hiroaki Suga, Tokyo (JP); Kenichiro Ito, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days. days.

(21) Appl. No.: 15/025,239

(22) PCT Filed: Oct. 15, 2014

(86) PCT No.: PCT/JP2014/077437
§ 371 (c)(1),
(2) Date: Mar. 25, 2016

(87) PCT Pub. No.: WO2015/056713
PCT Pub. Date: Apr. 23, 2015

(65) Prior Publication Data
US 2016/0237119 A1    Aug. 18, 2016

(30) Foreign Application Priority Data

Oct. 15, 2013 (JP) .................. 2013-214771

(51) Int. Cl.
| C07K 7/08 | (2006.01) |
| --- | --- |
| A61K 38/00 | (2006.01) |
| C07K 1/107 | (2006.01) |
| C07K 14/71 | (2006.01) |
| C07K 1/00 | (2006.01) |

(52) U.S. Cl.
CPC ............ C07K 7/08 (2013.01); A61K 38/00 (2013.01); C07K 1/00 (2013.01); C07K 1/1075 (2013.01); C07K 14/71 (2013.01); C07K 2319/00 (2013.01)

(58) Field of Classification Search
CPC ........ A61K 38/00; A61K 38/10; C07K 14/71; C07K 1/00; C07K 1/1075; C07K 2319/00; C07K 7/08
USPC ................. 514/21.5; 530/326, 327
See application file for complete search history.

(56) References Cited

U.S. PATENT DOCUMENTS

| 5,612,037 | A | 3/1997 | Huebner et al. | |
| --- | --- | --- | --- | --- |
| 6,809,175 | B1 * | 10/2004 | Forssmann | C07K 14/705 435/69.1 |
| 7,041,814 | B1 * | 5/2006 | Weinstock | C07K 14/265 435/252.3 |
| 9,029,636 | B2 * | 5/2015 | Wu | C07K 14/415 435/419 |
| 2010/0168380 | A1 | 7/2010 | Suga et al. | |
| 2012/0010153 | A1 | 1/2012 | Koltermann | |
| 2013/0041133 | A1 | 2/2013 | Aaronson et al. | |
| 2013/0316910 | A1 | 11/2013 | Suga et al. | |
| 2014/0377290 | A1 | 12/2014 | Kim et al. | |

FOREIGN PATENT DOCUMENTS

| JP | 10-503494 A | 3/1998 |
| --- | --- | --- |
| JP | 2012-515144 A | 7/2012 |
| JP | 2013-523149 A1 | 6/2013 |
| JP | 2015-503554 A | 2/2015 |
| WO | 2002051869 A1 | 7/2002 |
| WO | 2008117833 A1 | 10/2008 |
| WO | 2010-089019 A1 | 8/2010 |
| WO | 2012012352 A1 | 1/2012 |
| WO | 2012074129 A1 | 6/2012 |

OTHER PUBLICATIONS

Lam et al, "The role of HGF/c_MET signaling pathway in lymphoma," Journal of Hematology & Oncology, 2016, 9: 1-8.*
International Search Report received in PCT/JP2014/077437, dated Dec. 16, 2014.
Murakami, et al, "A Versatile tRNA Aminoacylation Catalyst Based on RNA" (2003) pp. 655-662, vol. 10, No. 7, Publisher: Chemistry & Biology.
White, et al., "On-resin N-methylation of cyclic peptides for discovery of orally bioavailable scaffolds", Sep. 29, 2011, pp. 810-817, vol. 7, No. 11, Publisher: Nature Chemical Biology.
Written Opinion received in PCT/JP2014/077437, dated Dec. 16, 2014.
Ito, et al., "Technologies for the synthesis of mRNA-encoding libraries and discovery of bioactive natural product-inspired non-traditional macrocyclic peptides", Mar. 18, 2013, pp. 3502-3528, vol. 18, No. 3, Publisher: Molecules.
Ito, et al., "Artificial Human Met Agonists Based on Macrocycle Scaffolds", Mar. 11, 2015, pp. 6373, vol. 6, Publisher: Nature Communications.
Jones, et al., "Engineering hepatocyte growth factor fragments with high stability and activity as Met receptor agonists and antagonists", Aug. 9, 2011, pp. 13035-13040, vol. 108, No. 32, Publisher: PNAS USA.
Liu, et al., "An engineered dimeric fragment of hepatocyte growth factor is a potent c-MET agonist", Nov. 21, 2014, pp. 4831-4837, vol. 588, No. 24, Publisher: FEBS letters.
Nakamura, et al., "The Discovery of Hepatocyte Growth Factor (HGF) and Its Significance for Cell Biology, Life Sciences and Clinical Medicine", Jan. 1, 2010, pp. 588-610, vol. 88, No. 6, Publisher: Proceedings of the Japan Academy. Series B, Physical and Biological Sciences.
Ido, et al., "Theme of the Month—Prospect of regenerative medicine using hepatocyte growth factors (HGF)", 2002, pp. 1436-1442, vol. 99, Publisher: Journal of Japanese Society of Gastroenterology.
Matsumoto, et al., "Prospects of tissue regeneration and regenerative medicine using HGF (hepatocyte growth factors)", 2005, pp. E202-E203, Publisher: Abstracts of Research Presentation Lecture, The Society of Chemical Engineers, SCEJ 37tj Autumn Meeting.
Chatterjee, et al., "Synthesis of N-methylated cyclic peptides", Feb. 9, 2012, pp. 432-444, vol. 7, No. 3, Publisher: Nature Protocols.

(Continued)

Primary Examiner — Julie Ha
(74) Attorney, Agent, or Firm — Suzannah K. Sundby, Esq.; Canady + Lortz LLP

(57) ABSTRACT

A peptide functioning as a c-Met agonist is described. A peptide complex comprising two or more peptides that bind to a c-Met protein and a linker that links the two or more peptides to one another is described. Such a peptide complex promotes autophosphorylation of the c-Met protein and induces cell growth.

9 Claims, 6 Drawing Sheets

(56) References Cited

OTHER PUBLICATIONS

Goto, et al., "Reprogramming the translation initiation for the synthesis of physiologically stable cyclic peptides", Feb. 15, 2008, pp. 120-129, vol. 3, No. 2, Publisher: ACS Chemical Biology.

Kawakami, et al., "Diverse backbone-cyclized peptides via codon reprogramming", Dec. 1, 2009, pp. 888-890, vol. 5, No. 12, Publisher: Nature Chemical Biology.

Kawakami, et al., "Messenger RNA-Programmed Incorporation of Multiple N-Methyl-Amino Acids into Linear and Cyclic Peptides", Jan. 25, 2008, pp. 32-42, vol. 15, No. 1, Publisher: Chemistry and Biology.

Murakami, et al., "A versatile tRNA aminoacylation catalyst based on RNA", Jul. 1, 2003, pp. 655-662, vol. 10, No. 7, Publisher: Chemistry and Biology.

Sako, et al., "Ribosomal synthesis of Bicyclic Peptides via Two Orthogonal Inter-Side-Chain Reactions", Jan. 1, 2008, pp. 7232-7234, vol. 130, No. 23, Publisher: Journal of the American Chemical Society.

Supplemental European Search Report and European Search Opinion received in EP3059244 dated Sep. 27, 2017.

Yamagishi, "Ribosomal Synthesis of Cyclic Peptides with a Fluorogenic Oxidative Coupling Reaction", Jun. 6, 2009, pp. 1469-1472, vol. 10, No. 9, Publisher: ChemBioChem.

* cited by examiner

C-MET PROTEIN AGONIST

REFERENCE TO A SEQUENCE LISTING SUBMITTED VIA EFS-WEB

The content of the ASCII text file of the sequence listing named "20160325_034574_010US1_seq" which is 14.2 kb in size was created on Oct. 15, 2014 and electronically submitted via EFS-Web herewith this U.S. National Phase application is incorporated herein by reference in its entirety.

TECHNICAL FIELD

The present invention relates to a peptide complex serving as a c-Met protein agonist, and the like.

BACKGROUND ART c-Met, a hepatocyte growth factor (HGF) receptor, is one of receptor tyrosine kinases. It dimerizes when HGF binds thereto and then, autophosphorylation of the tyrosine residue occurs. As a result, signaling of the MAPK pathway or Akt pathway is activated and cell growth is promoted, while induction of cell apoptosis is inhibited. These phenomena may cause canceration of cells so that c-Met is expected as a potent molecular target in cancer therapy. In fact, various anticancer agents targeting HGF or c-Met are under development.

In recent years, a variety of peptide drugs have been researched and developed. Due to chemical and biological diversity, peptide drugs tend to have higher specificity than low molecular compounds in interaction with target molecules. As a result, they can obtain greater physiological activity.

On the other hand, peptide drugs are likely to be degraded in a short time because of inferiority in protease resistance to large proteins such as antibiotics. Improvement in such a problem of peptide drugs has been investigated recently by adding various modifications to them.

The present inventors has developed artificial aminoacylated RNA catalyst "flexizyme" (for example, Non-patent Document 1) so far. Flexizyme is an artificial RNA catalyst having aminoacyl tRNA synthetase-like activity and it is capable of linking an arbitrary amino acid to an arbitrary tRNA. Using flexizyme enables binding of a desired amino acid to a tRNA having a desired anticodon so that a genetic code table can be reprogrammed by making an amino acid correspond to an arbitrary codon different from that of a natural genetic code. This is called "codon reassignment".

Codon reassignment using flexizyme makes it possible to introduce an arbitrary amino acid including a non-proteinogenic amino acid into an arbitrary position of a peptide. The resulting peptide may have enhanced protease resistance, cellular permeability, or affinity or specificity for a target molecule.

In recent years, on the other hand, macrocyclization of peptides has attracted attentions. Macrocyclic peptides can be found in the natural world and they are known to have stable conformation. Due to their size and complexity, macrocyclic peptides are known to show specificity higher than that of small non-cyclized peptides (for example, Non-Patent Document 2) and are expected to serve as an inhibitor against highly difficult targets such as molecules whose protein-protein interaction is unknown, or molecules whose binding site for a low molecular compound is unknown. Constraint by the cyclic structure is thought to improve the bioavailability of peptides or their resistance against metabolism.

In the study of providing various modifications to peptides as described above, there is a demand for the development of peptides excellent in resistance against metabolism or stability in vivo.

PRIOR ART DOCUMENT

Non-Patent Document

Non-Patent Document 1: H. Murakami, H. Saito, and H. Suga, (2003), Chemistry & Biology, Vol. 10, 655-662.
Non-Patent Document 2: White, T. R. et al., Nature chemical biology, 7(11), 810-7.

SUMMARY OF THE INVENTION

Problem to be Solved

As described above, c-Met has a function of promoting cell growth activity or cell migration activity so that it has attracted attentions as a target of anticancer agents. On the contrary, if this function can be enhanced to promote cell growth or migration, there is a possibility of promoting production of cell preparations to be used for regenerative therapy or recovery from refractory organ diseases such as cirrhosis.

An object of the present invention is therefore to provide a peptide functioning as a c-Met agonist.

Solution to Problem

With a view to achieving the above object, the present inventors have made a macrocyclic peptide library and by screening using the library, found a macrocyclic peptide that binds to c-Met. It has been verified that when a peptide complex is formed by linking two macrocyclic peptides that bind to c-Met, the macrocyclic peptides of such a peptide complex promote autophosphorylation of c-Met proteins and activate a c-Met signaling pathway.

Further, it has been verified in vitro that this peptide complex actually promotes cell growth or cell migration, leading to completion of the present invention.

The present invention therefore relates to:

[1] a peptide complex comprising two or more peptides that bind to c-Met proteins; and a linker that links these two or more peptides to one another;

[2] the peptide complex according to [1] above, wherein each of the two or more peptides that bind to c-Met proteins is macrocyclized;

[3] the peptide complex according to [1] or [2] above, wherein the two or more peptides that bind to c-Met proteins are each independently selected from the group consisting of the following (i) to (vii):

(i)
ISWNEFNSPNWRFIT;
(SEQ ID NO: 1)

(ii)
RQFNRRTHEVWNLD;
(SEQ ID NO: 2)

(iii)
WYYAWDQTYKAFP;
(SEQ ID NO: 3)

(iv) a peptide that has any of the amino acid sequences (i) to (iii) in which one or several amino acids have been substituted and binds to a c-Met protein;
(v) a peptide that has 80% or more sequence identity with any of the amino acid sequences (i) to (iii) and binds to a c-Met protein; and
(vi) a peptide that has any of the amino acid sequences (i) to (v) in which at least one amino acid has been modified;

[4] the peptide complex according to [3] above, wherein the two or more peptides that bind to c-Met proteins have, at the terminal or non-terminal thereof, an amino acid residue for macrocyclizing the peptides;

[5] the peptide complex as described above in any one of [1] to [4], wherein the linker is selected from the group consisting of BMH, Bis-MAL-PEG3, and Bis-MAL-PEG11;

[6] a c-Met protein agonist comprising the peptide complex according to any one of [1] to [5] above;

[7] a pharmaceutical composition comprising the peptide complex according to any one of [1] to [5] above;

[8] the pharmaceutical composition according to [7] above, for treating or preventing a disease selected from the group consisting of acute hepatitis, fulminant hepatitis, cirrhosis, biliary atresia, fatty liver, acute renal insufficiency, chronic renal insufficiency, diabetic nephropathy, acute pneumonia, pulmonary fibrosis, angiopathy, myocardial infarction, dilated cardiomyopathy, skin ulcer, cerebral infarction, and amyotrophic lateral sclerosis;

[9] a protecting agent or regeneration promoting agent of an organ after organ transplantation, comprising the peptide complex according to any one of [1] to [5] above;

[10] a method for producing a peptide that binds to a target substance and has high stability, comprising following steps:
N-methylating or N-alkylating at least one amino acid residue of a peptide that binds to the target substance,
cyclizing the peptide; and
evaluating the stability of the peptide;

[11] the method according to [10] above, wherein the steps from the step of N-methylating or N-alkylating an amino acid residue to the step of evaluating the stability of the peptide are repeated to comprehensively study the influence of the N-methylation or N-alkylation on all the amino acids;

[12] the method according to [10] above, wherein the amino acid residue in the step of N-methylating or N-alkylating is the following:
an arginine residue;
a lysine residue;
an amino acid residue within 2 amino acids from an arginine residue or lysine residue;
an arginine residue or lysine residue that is in a region of two or more consecutive amino acids selected from the group consisting of arginine residues and lysine residues; or
an amino acid residue within 2 amino acids from an of arginine residue and lysine residue in a region of two or more consecutive amino acids selected from the group consisting of arginine residues and lysine residues; and

[13] the method according to any one of [10] to [12] above, wherein the evaluating the stability of the peptide includes measuring protease resistance of the peptide.

Advantageous Effects of Invention

The peptide complex according to the present invention can promote cell growth or cell migration through promotion of autophosphorylation of c-Met. It is therefore useful for chronic fibrous diseases that decrease HGF expression or as a protecting agent or regeneration promoting agent of an organ during organ transplantation or as a production promoter of a cell preparation to be used in regenerative therapy.

DESCRIPTION OF EMBODIMENTS

Peptide Complex

Figure 1:
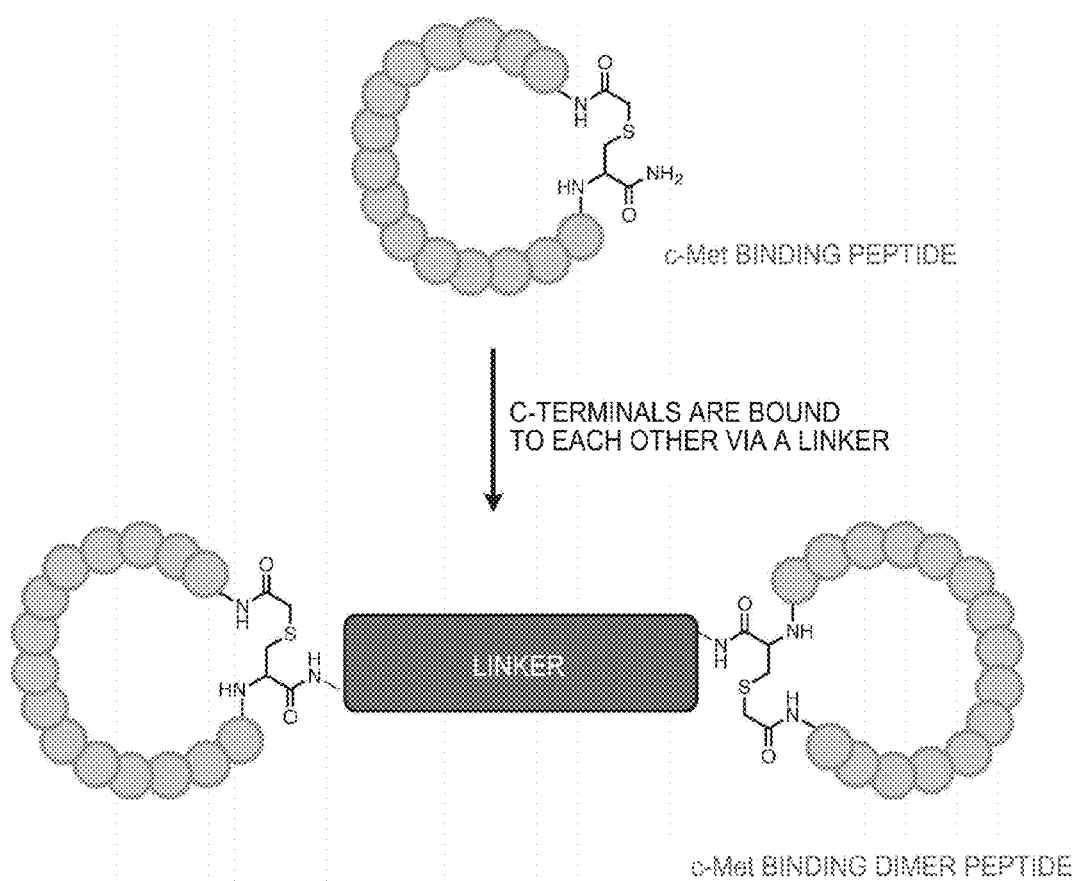
FIG. 1 is a schematic view showing an example of a c-Met binding dimeric peptide (peptide complex according to the present invention).

The peptide complex according to the present invention is composed of two or more peptides that respectively bind to c-Met proteins (human protein has GenBank Accession No. NP_000236 and murine protein has NP_032617) and a linker that links them to one another.

The c-Met protein is a hepatocyte growth factor (HGF) receptor and has tyrosine kinase activity. The c-Met protein is a transmembrane type receptor composed of α and β sub-units bound to each other via a disulfide bond. In vivo, binding of HGF to the c-Met protein causes dimerization and then, autophosphorylation of the c-Met protein. As a result, various signal transduction systems are activated.

The peptide complex according to the present invention promotes autophosphorylation of c-Met proteins. In the peptide complex according to the present invention, two or more c-Met protein-binding peptides are linked to one another via a linker. Autophosphorylation is presumed to occur because two or more peptides are respectively bound to c-Met proteins, and the two or more c-Met proteins are physically attracted to one another to form a multimer.

The peptide complex according to the present invention contains two or more c-Met protein-binding peptides. The number of the peptides is not limited insofar as it is two or more. It may be, for example, 3, 4, 5, 6, 7, 8, 9, or 10 or it may be 20 or more, 30 or more, 50 or more, 100 or more, or even more. When the number of the c-Met binding protein peptides is two, two peptides bind to c-Met proteins, respectively, and as a result, these two c-Met proteins are physically attracted to each other to form a dimer, causing autophosphorylation.

In the peptide complex, the peptides may be linked in any form by a linker. For example, when a peptide complex contains two c-Met protein-binding peptides, the peptide complex may be in a dumbbell form in which a linker has, at both ends thereof, c-Met protein-binding peptides. The peptide complex having a large number of c-Met protein-binding peptides may be in dendrimer form.

As used herein, the "peptides that bind to c-Met proteins (c-Met protein-binding peptides)" may be any peptide insofar as a peptide complex prepared using them promotes autophosphorylation of c-Met proteins. The number of amino acids of the c-Met protein-binding peptide is not particularly limited, but it may be, for example, 4 or more, 5 or more, 8 or more, 10 or more, 20 or less, 25 or less, or 30 or less.

In the present specification, the term "amino acid" is used in its broadest meaning and it encompasses not only natural amino acids but also artificial amino acid variants and derivatives of them. The amino acids may be represented by a commonly used single-letter or three-letter code. As used herein, examples of the amino acid or derivatives thereof include natural proteinogenic L-amino acids, unnatural amino acids, and chemically synthesized compounds having properties known in the art as characteristics of an amino acid. Examples of the unnatural amino acids include, but not limited to, α,α-disubstituted amino acids (such as α-methylalanine), N-alkyl-α-amino acids, D-amino acids, β-amino acids, and α-hydroxy acids, each having a main chain structure different from that of natural amino acids; amino acids (such as norleucine and homohistidine) having a side-chain structure different from that of natural amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group.

The amino acids may be either proteinogenic amino acids or non-proteinogenic amino acids.

The term "proteinogenic amino acid" as used herein means an amino acid (Arg, His, Lys, Asp, Glu, Ser, Thr, Asn, Gln, Cys, Gly, Pro, Ala, Ile, Leu, Met, Phe, Trp, Tyr, or Val) that constitutes a protein.

The c-Met protein-binding peptide may be macrocyclized. Macrocyclization of the peptide is formed not only through binding between the N-terminal amino acid and the C-terminal amino acid but it may be formed by binding between the terminal amino acid and an amino acid other than the terminal one or binding between amino acids other than terminal ones.

When the C-terminal amino acid of the c-Met protein-binding peptide is not used for cyclization, this C terminal is not limited to a carboxyl group or a carboxylate group but may be an amide or ester. The c-Met protein-binding peptide of the present invention encompasses salts of the c-Met protein-binding peptide. Examples of the salts of the c-Met protein-binding peptide include salts with a physiologically acceptable base or acid such as inorganic acid (such as hydrochloric acid, hydrobromic acid, hydroiodic acid, sulfuric acid, or phosphoric acid) addition salts, organic acid (such as p-toluenesulfonic acid, methanesulfonic acid, oxalic acid, p-bromophenylsulfonic acid, carboxylic acid, succinic acid, citric acid, benzoic acid, or acetic acid) addition salts, inorganic bases (such as ammonium hydroxide, alkali or alkaline earth metal hydroxides, carbonates, or bicarbonates), and amino acid addition salts.

Specific examples of the c-Met protein-binding peptide include those having the following amino acid sequence:

(i)
    (SEQ ID NO: 1)
ISWNEFNSPNWRFIT;

(ii)
    (SEQ ID NO: 2)
RQFNRRTHEVWNLD;

(iii)
    (SEQ ID NO: 3)
WYYAWDQTYKAFP;

Examples of the c-Met protein-binding peptide also include peptides (iv) having any of the amino acid sequence represented by SEQ ID NOs: 1 to 3 in which one or several amino acids have been added, substituted or deleted and binding to a c-Met protein.

Although the number of amino acids to be added or the like is not particularly limited insofar as the peptide thus obtained binds to a c-Met protein, it may be, for example, 1, 2, 3, 4, or 5.

Examples of the c-Met protein-binding peptide also include peptides (v) having 80% or more sequence identity with any of the amino acid sequences represented by SEQ ID NOs: 1 to 3 and binding to a c-Met protein.

The sequence identity may be 85% or more, 90% or more, 95% or more, or 98% or more.

At least one of the amino acids of the c-Met protein-binding peptides (i) to (v) may be modified insofar as they can solve the problem of the present invention. Examples of the modification of the amino acid include phosphorylation, methylation, acetylation, adenylation, ADP ribosylation, and glycosylation.

As shown in Example, the peptide obtained by N-methylation of a given amino acid may have increased stability in serum while maintaining its affinity for a c-Met protein.

The c-Met protein-binding peptides of (i) to (vi) may further contain an amino acid residue (which will be described later in "ring-forming amino acid") for cyclizing the peptide. The amino acid for cyclizing the peptide may be placed at the N terminal and C terminal of the peptide or may be placed at the nonterminal thereof. When it is placed at the nonterminal of the peptide, it may be placed, for example, at the second amino acid residue, the third amino acid residue, or the fourth amino acid residue, each from the terminal.

The c-Met protein-binding peptides of (i) to (vi) may further contain an amino acid residue for binding a linker to the peptides. Examples of the amino acid for binding a linker to them include, but not limited to, a Cys residue placed at the C terminal thereof.

The kind or length of the linker to be used for the peptide complex according to the present invention is not particularly limited insofar as the resulting peptide complex promotes autophosphorylation of a c-Met protein. For example, polymers such as PEG, peptides, nucleic acids, and sugars, and combinations thereof may be used as the linker. The linker can be bound to the c-Met protein-binding peptide by a known method or a method based thereon.

Non-limiting examples of the linker include the following BMH, Bis-MAL-PEG3, and Bis-MAL-PEG11. These linkers can be bound to the c-Met protein-binding peptide through a Cys residue attached to the terminal of the c-Met protein-binding peptide.

[Chemical formula 1]

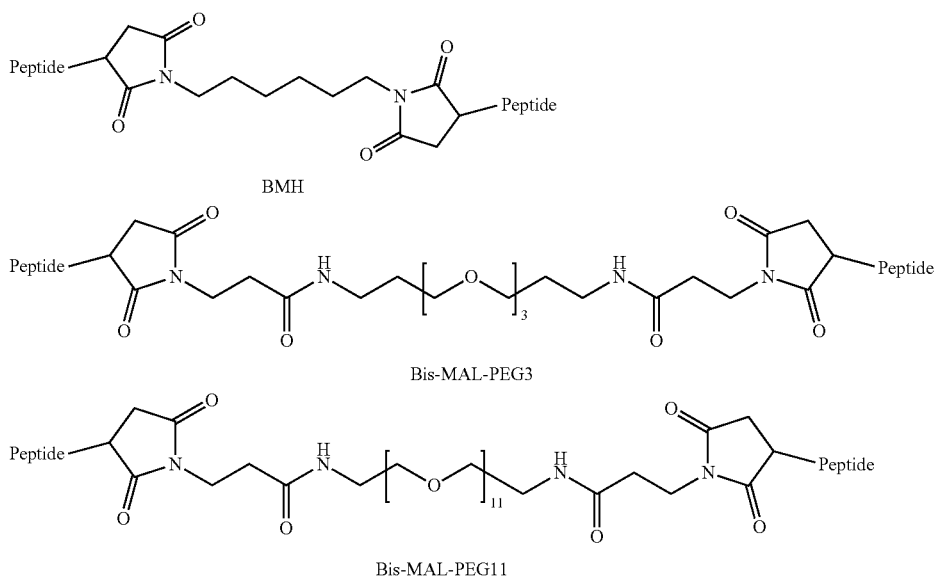

Two c-Met protein-binding peptides contained in the peptide complex according to the present invention may be either the same or different from each other.

(Nucleic Acid Encoding c-Met Protein-Binding Peptide)

The present invention encompasses a nucleic acid encoding the c-Met protein-binding peptide.

As used herein, the "nucleic acid" may be a natural or an unnatural one. Examples of the nucleic acid includes, but not limited to, DNA, RNA, and a chimera thereof.

(Production Process of Peptide Complex)

A production process of the peptide complex according to the present invention is not particularly limited. The peptide complex of the present invention can be produced, for example, by preparing c-Met protein-binding peptides by a known method or a method based on it, for example, chemical synthesis method such as liquid phase method, solid phase method, and hybrid method using liquid phase method and solid phase method in combination, genetic recombination method, or translational synthesis in a cell-free translation system, and then linking the resulting c-Met protein-binding peptides with an appropriate linker.

1. Translational Synthesis in Cell-Free Translation System

The c-Met protein-binding peptide according to the present invention can be prepared by preparing a nucleic acid encoding the peptide and translating the resulting nucleic acid in a cell-free translation system. The nucleic acid encoding the c-Met protein-binding peptide can be designed as appropriate by those skilled in the art by using a genetic code used in in vivo translation system, a reprogrammed genetic code, or a combination thereof. The nucleic acid may be either DNA or RNA.

In accordance with the method using a cell-free translation system, not only a natural amino acid but also an unnatural amino acid can be introduced efficiently into a peptide by using tRNA aminoacylated with the unnatural amino acid. For example, when artificial aminoacyl tRNA synthetase flexizyme developed by the present inventors is used, tRNA having an arbitrary anticodon can be aminoacylated with an arbitrary natural or unnatural amino acid. By using this technology, therefore, it is possible to reprogram a genetic code made of an mRNA triplet so that it encodes an amino acid different from that of in vivo translation system (WO2008/059823).

For example, an initiator codon AUG encodes formylmethionine and methionine in prokaryotic cells and eukaryotic cells, respectively. When flexizyme is used, on the other hand, tRNA corresponding to an initiator codon can be aminoacylated with another amino acid so that peptide synthesis can be initiated by an arbitrary amino acid. In addition, tRNA corresponding to a codon other than the initiator codon can be aminoacylated with an arbitrary amino acid so that the arbitrary amino acid can be introduced into an arbitrary position of a peptide using a cell-free translation system.

When flexizyme is used, not only an amino acid but also a hydroxy acid or carboxylic acid can be bound to tRNA. Therefore, an arbitrary hydroxy acid or carboxylic acid can also be introduced into an arbitrary position of a peptide using a cell-free translation system. The macrocyclic peptide of the present invention may therefore have a hydroxy acid or carboxylic acid introduced instead of an amino acid.

As flexizyme, for example, those described in the following documents are known:

H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature methods 3, 357-359; N. Niwa, Y. Yamagishi, H. Murakami, H. Suga, (2009) Bioorganic & Medicinal Chemistry Letters 19, 3892-3894; and WO2007/066627.

As flexizyme, original flexizyme (Fx) and altered ones thereof such as dinitrobenzyl flexizyme (dFx), enhanced flexizyme (eFx), and aminoflexizyme (aFx) are also known.

The aminoacylation method of an arbitrary tRNA with an arbitrary amino acid is not limited to a method using flexizyme and other method can also be applied to the present invention.

Non-limiting examples of unnatural amino acids that can be introduced using flexizyme are shown below. In the following table, DBE and CME are the type of esters when these amino acids are bound to tRNA by using flexizyme and DBE represents 3,5-dinitrobenzyl ester and CME represents cyanomethyl ester.

TABLE 1

Initiator amino acids

| | |
|---|---|
| Acetyl-L-alanine | DBE |
| Acetyl-L-phenylalanine | CME |
| Acetyl-L-tyrosine | CME |
| Acetyl-L-tryptophan | CME |
| Acetyl-D-alanine | DBE |
| Acetyl-D-phenylalanine | CME |
| Acetyl-D-tyrosine | CME |
| Acetyl-D-tryptophan | CME |
| N-Chloroacetyl-L-alanine | DBE |
| N-Chloroacetyl-L-phenylalanine | CME |
| N-Chloroacetyl-L-tyrosine | CME |
| N-Chloroacetyl-L-tryptophan | CME |
| N-Chloroacetyl-D-alanine | DBE |
| N-Chloroacetyl-D-phenylalanine | CME |
| N-Chloroacetyl-D-tyrosine | CME |
| N-Chloroacetyl-D-tryptophan | CME |
| N-3-chloromethylbenzoyl-L-tyrosine | CME |
| N-3-chloromethylbenzoyl-L-tryptophane | CME |

TABLE 2

Amino acids that crosslink in peptides

| | |
|---|---|
| Nγ-(2-chloroacetyl)-α,γ-diaminobutylic acid | DBE |
| Nγ-(2-chloroacetyl)-α,γ-diaminopropanoic acid | DBE |

TABLE 3

D-amino acids

| | |
|---|---|
| D-Serine | DBE |
| D-Phenylalanine | CME |
| D-Tyrosine | CME |
| D-Tryptophan | CME |

TABLE 4

N-methylamino acids

| | |
|---|---|
| N-methyl-Glycine | DBE |
| N-methyl-Alanine | DBE |
| N-methyl-Serine | DBE |
| N-methyl-Histidine | DBE |
| N-methyl-Phenylalanine | CME |
| N-methyl-Tyrosine | CME |
| N-methyl-Tryptophan | CME |

TABLE 5

Peptoid blocks

| | |
|---|---|
| N-ethyl-Glycine | DBE |
| N-n-propyl-Glycine | DBE |
| N-n-butyl-Glycine | DBE |
| N-n-pentyl-Glycine | DBE |

TABLE 5-continued

Peptoid blocks

| | |
|---|---|
| N-n-hexyl-Glycine | DBE |
| N-n-heptyl-Glycine | DBE |
| N-n-octyl-Glycine | DBE |
| N-isopentyl-Glycine | DBE |
| N-(2-phenylethyl)-Glycine | CME |
| N-(3-phenylpropyl)-Glycine | CME |
| N-[2-(p-hydroxyphenyl)ethyl]-Glycine | CME |

TABLE 6

Other special amino acids

| | |
|---|---|
| p-biphenylalanine | CME |
| p-trifluoromethylphenylalanine | CME |
| p-azidophenylalanine | CME |
| p-biotinyl-aminophenylalanine | CME |
| e-N-Biotinyl-lysine | DBE |
| e-N-Acetyl-lysine | DBE |
| L-Citrulline | DBE |
| L-5-Hydroxytryptphan | CME |
| L-1,2,3,4,-Tetrahydroisoquinoline-3-carboxylic acid | DBE |
| Aminoisobutyric acid | DBE |
| N-methyl-aminoisobutyric acid | DBE |
| N-methyl-Phenylglycine | CME |

As used herein, the "cell-free translation system" is also called "cell-free protein synthesis system. It is a translation system wherein cells such as *Escherichia coli* are not used as they are, but components presented in cells such as *Escherichia coli* are used. This system includes a system using mainly a cell extract and a system (re-constituted cell-free translation system) using a reaction liquid reconstituted of purified components of the cell extract. By the cell-free translation system, a high-purity expression product can be obtained without purification.

Examples of the system using mainly a cell extract include systems using an *Escherichia coli* extract, a wheat germ extract, a rabbit reticulocyte extract, or an insect cell extract.

The reconstituted cell-free translation system can be constructed of a ribosome protein, aminoacyl tRNA synthetase (ARS), ribosomal RNA, amino acid, rRNA, GTP, ATP, translation initiation factor (IF), elongation factor (EF), termination factor (RF), and ribosome regeneration factor, other factors necessary for translation, and the like, each purified in advance.

These translation systems may also be supplied continuously with energy by means of dialysis. An RNA polymerase may be added to them for carrying out transcription from DNA.

Examples of a commercially available cell-free translation system include *Escherichia-coli* derived systems such as RTS-100 (registered trademark) of Roche Diagnostics, systems using a wheat germ extract such as those of ZOE-GENE Corporation or CellFree Sciences, and reconstituted translation systems such as PURESYSTEM (registered trade mark) of PGI and PUREXPRESS (registered trademark) In Vitro Protein Synthesis Kit of New England BioLabs.

As a system using a ribosome of *Escherichia coli*, for example, technologies described in the following documents are known and they may be used.

H. F. Kung et al., 1997. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

When the reconstituted translation system is used, constituting components of the translation system can be selected freely, depending on the purpose of use. When a translation system that does not contain a specific amino acid or a translation system not that does not contain an aminoacyl tRNA corresponding to a specific amino acid and therefore incapable of producing the aminoacyl tRNA is reconstituted, a tRNA that decodes a codon corresponding to the amino acid will not be presented in the system. Here, by aminoacylating a tRNA having an anticodon corresponding to the codon with a desired amino acid by using flexizyme or the like and then adding it to the translation system, the desired amino acid can be introduced into a peptide with the codon.

A FIT system used in Example which will be described later is one example of re-constituted translation systems for efficiently reprogramming a genetic code developed by the present inventors.

By using the above-mentioned technology, an amino acid necessary for the formation of a ring or a modified amino acid can also be introduced into a desired position of the c-Met protein-binding peptide of the present invention.

In this case, codons that encode two amino acids (which may hereinafter be called "ring-forming amino acids") necessary for ring formation are introduced into a nucleic acid that encodes the c-Met protein-binding peptide.

Although a method of macrocyclizing a peptide is not particularly limited, a translationally synthesized peptide can be macrocyclized by a spontaneous reaction by incorporating, for example, an amino acid having the functional group 1 shown below and an amino acid having the functional group 2 corresponding thereto. Either the functional group 1 or 2 may be placed on the N-terminal side; they may be placed at the N-terminal and C-terminal, respectively; one of them may be a terminal amino acid and the other one may be a non-terminal amino acid; or both may be non-terminal amino acids.

TABLE 7

| | Functional group 1 | Functional group 2 |
|---|---|---|
| (A) | —C(=O)—CH$_2$—X$_1$ (A-1) | HS— (A-2) |
| (B) | —C≡C—H (B-1) | N$_3$— (B-2) |
| (C) | —Ar—CH$_2$NH$_2$ (C-1) | HO-(5-hydroxyindole) (C-2) |
| (D) | —C≡C—CH$_2$—X$_1$ (D-1) | HS— (D-2) |
| (E) | —Ar—CH$_2$—X$_1$ (E-1) | HS— (E-2) |

In the above formulas, X$_1$ represents Cl, Br, or I and Ar represents an optionally substituted aromatic ring.

As the amino acid having the functional group of (A-1), for example, a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophane, β-N-chloroacetyl-L-diaminopropanoic acid, γ-N-chloroacetyl-L-diaminobutyric acid, α-N-chloroacetyl-L-ornithine, and ε-N-chloroacetyl-L-lysine, and D-amino acid derivatives corresponding thereto.

Examples of amino acids having the functional group (A-2) include cysteine, homocysteine, mercaptonorvaline, mercaptonorleucine, 2-amino-7-mercaptoheptanoic acid, 2-amino-8-mercaptooctanoic acid, amino acids obtained by protecting the SH group of these amino acids and then eliminating the protecting group, and D-amino acid derivatives corresponding thereto.

The cyclization method may be carried out according to the method described, for example, in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); and Kawakami T. et al, Chemistry & Biology 15, 32-42 (2008), and WO2008/117833.

As amino acids having the functional group (B-1), for example, propargylglycine, homopropargylglycine, 2-amino-6-heptynoic acid, 2-amino-7-octynoic acid, and 2-amino-8-nonynoic acid can be used. In addition, 4-pentynoylated or 5-hexynoylated amino acids can also be used. Examples of the 4-pentynoylated amino acids include N-(4-pentenoyl)-L-alanine, N-(4-pentenoyl)-L-phenylalanine, N-(4-pentenoyl)-L-tyrosine, N-(4-pentenoyl)-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophan, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

As amino acids having the functional group (B-2), for example, azidoalanine, 2-amino-4-azidobutanoic acid, azidoptonorvaline, azidonorleucine, 2-amino-7-azidoheptanoic acid, and 2-amino-8-azidooctanoic acid can be used. Azidoacetylated or 3-azidopentanoylated amino acids can also be used. Examples of the azidoacetylated amino acids include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophan, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

The cyclization method can be performed according to the method described, for example, in Sako, Y. et al., Journal of American Chemical Society 130, 7932-7934 (2008) or WO2008/117833.

Examples of amino acids having the functional group (C-1) include N-(4-aminomethyl-benzoyl)-phenylalanine (AMBF) and 4-3-aminomethyltyrosine.

Examples of amino acids having the functional group (C-2) include 5-hydroxytryptophan (W$_{OH}$).

The cyclization method can be performed according to the method described, for example, in Yamagishi, Y. et al., ChemBioChem 10, 1469-1472 (2009) or WO2008/117833.

Examples of amino acids having the functional group (D-1) include 2-amino-6-chloro-hexynoic acid, 2-amino-7-chloro-heptynoic acid, and 2-amino-8-chloro-octynoic acid.

Examples of amino acids having the functional group (D-2) include cysteine, homocysteine, mercaptonorvaline, mercaptonorleucine, 2-amino-7-mercaptoheptanoic acid, and 2-amino-8-mercaptooctanoic acid, amino acids obtained by protecting the SH group of these amino acids and then eliminating the protecting group, and D-amino acid derivatives corresponding thereto.

The cyclization method can be performed according to the method described, for example, in WO2012/074129.

Examples of the amino acid (E-1) include N-3-chloromethylbenzoyl-L-phenylalanine, N-3-chloromethylbenzoyl-L-tyrosine, and N-3-chloromethylbenzoyl-L-tryptophane.

Examples of the amino acid (E-2) include cysteine, homocysteine, mercaptonorvaline, mercaptonorleucine, 2-amino-7-mercaptoheptanoic acid, and 2-amino-8-mercaptooctanoic acid, and amino acids obtained by protecting the SH group of these amino acids and then eliminating the protecting group, and D-amino acid derivatives corresponding thereto.

2. Synthesis by Solid-Phase Method

The c-Met protein-binding peptide according to the present invention can also be prepared by solid-phase synthesis.

In solid-phase method, an esterification reaction is performed, for example, between the hydroxyl group of a hydroxyl-containing resin and the carboxyl group of a first amino acid (usually, C-terminal amino acid of an intended peptide) having an α-amino group protected with a protecting group. As the esterifying catalyst, a known dehydration condensation agent such as 1-mesitylenesulfonyl-3-nitro-1, 2,4-triazole (MSNT), dicyclohexylcarbodiimide (DCC), or diisopropylcarbodiimide (DIPCDI) may be used.

Next, the protecting group of the α-amino group of the first amino acid is eliminated and at the same time, a second amino acid having all the functional groups protected except the main chain carboxyl group is added and then, the carboxyl group is activated to bind the first and second amino acids to each other. Then, the α-amino group of the second amino acid is deprotected and a third amino acid having all the functional groups protected except the main chain carboxyl group is added. The carboxyl group is then activated to bind the second and third amino acids to each other. The above-described reactions are repeated to synthesize a peptide having an intended length. Then, all the functional groups are deprotected.

Examples of the resin for solid-phase synthesis include Merrifield resin, MBHA resin, Cl-Trt resin, SASRIN resin, Wang resin, Rink amide resin, HMFS resin, Amino-PEGA resin (Merck), and HMPA-PEGA resin (Merck). These resins may be provided for use after washed with a solvent (dimethylformamide (DMF), 2-propanol, methylene chloride, or the like).

Examples of the protecting group of the α-amino acid include a benzyloxycarbonyl (Cbz or Z) group, a tert-butoxycarbonyl (Boc) group, a fluorenylmethoxycarbonyl (Fmoc) group, a benzyl group, an allyl group, and an allyloxycarbonyl (Alloc) group. The Cbz group can be removed using hydrofluoric acid, hydrogenation, or the like; the Boc group can be removed using trifluoroacetic acid (TFA); and the Fmoc group can be removed by the treatment with piperidine.

For protection of the α-carboxyl group, a methyl ester, an ethyl ester, a benzyl ester, a tert-butyl ester, a cyclohexyl ester, or the like may be used.

As to other functional groups of an amino acid, the hydroxyl group of serine or threonine can be protected with a benzyl group or a tert-butyl group and the hydroxyl group of tyrosine can be protected with a 2-bromobenzyloxycarbonyl group or a tert-butyl group. The amino group of a lysine side chain or the carboxyl group of glutamic acid or aspartic acid can be protected similarly to the α-amino group or α-carboxyl group.

The carboxyl group can be activated with a condensation agent. Examples of the condensation agent include dicyclohexylcarbodiimide (DCC), diisopropylcarbodiimide (DIPCDI), 1-ethyl-3-(3-dimethylaminopropyl)carbodiimide (EDC or WSC), (1H-benzotriazol-1-yloxy)tris(dimethylamino)phosphonium hexafluorophosphate (BOP), and 1-[bis(dimethylamino)methyl]-1H-benzotriazolium-3-oxide hexafluorophosphate (HBTU).

A peptide chain can be cleaved from the resin by treating it with an acid such as TFA or hydrogen fluoride (HF).

The step of linking the c-Met protein-binding peptides via a linker can be performed by those skilled in the art by a known method for linking the linker to the peptide or a method based thereon, depending on the kind of the linker.

For example, when the linker is any of the above-mentioned BMH, Bis-MAL-PEG3, and Bis-MAL-PEG11, it may be bound to the c-Met protein-binding peptide by attaching a Cys residue to the terminal of the c-Met protein-binding peptide in advance.

When the linker is a peptide, a nucleic acid encoding two or more c-Met protein-binding peptides may be linked with a nucleic acid encoding a linker peptide to express a fusion protein of the c-Met protein-binding peptides and the linker peptide.

The peptide complex according to the present invention acquires an HGF-like function through multimerization of the c-Met protein and promotion of autophosphorylation caused thereby.

The peptide complex according to the present invention is therefore useful as a c-Met agonist or a pharmaceutical composition. In addition, it can be used in vitro or in vivo as a protecting agent or regeneration promoting agent of an organ at the time of organ transplantation.

The pharmaceutical composition according to the present invention contains the peptide complex according to the present invention as an active ingredient. Having an HGF-like function, it is useful for cell growth promotion, cell migration promotion, apoptosis suppression, morphogenesis induction, vascularization, or regeneration or protection of tissue or organ and is therefore used as a therapeutic or preventive agent for diseases associated with them.

Examples of such diseases include, but not limited to, acute hepatitis, fulminant hepatitis, cirrhosis, biliary atresia, fatty liver, acute renal insufficiency, chronic renal insufficiency, diabetic nephropathy, acute pneumonia, pulmonary fibrosis, angiopathy, myocardial infarction, dilated cardiomyopathy, skin ulcer, cerebral infarction, and amyotrophic lateral sclerosis.

The administration route of the pharmaceutical composition is not particularly limited and it may be administered either orally or parenterally. Examples of the parenteral administration include administration by injection such as intramuscular, intravenous, or subcutaneous injection, transdermal administration, and transmucosal administration (nasal, buccal, ocular, pulmonary, vaginal, or rectal).

Since the peptide in the pharmaceutical composition is readily metabolized and excreted, it can be subjected to various modifications. For example, a polypeptide added with polyethylene glycol (PEG) or sugar chain can have longer residence time in blood and reduced antigenicity. A polypeptide may be encapsulated using a sustained-release base such as an emulsion, nanoparticles, nanospheres, prepared from a biodegradable polymer compound such as polylactic acid glycol (PLGA), porous hydroxyapatite, liposome, surface-modified liposome, or unsaturated fatty acid. When it is administered transdermally, it can be penetrated through the stratum corneum by passing a weak electrical current through the skin surface (iontophoresis).

With regard to the pharmaceutical composition, the active ingredient thereof may be used as it is, or it can be for formulated by adding thereto a pharmaceutically acceptable carrier, excipient, additive, or the like. Examples of the dosage form include liquids and solutions (for example, injections), dispersions, suspensions, tablets, pills, powders, suppositories, powders, fine granules, granules, capsules, syrups, troches, inhalants, ointments, ophthalmic preparations, nasal preparations, ear preparations, and cataplasms.

The formulation can be obtained in a conventional manner by using, for example, an excipient, a binder, a disintegrant, a lubricant, a dissolving agent, a solubilizing agent, a colorant, a taste/odor corrigent, a stabilizer, an emulsifier, an absorption promoter, a surfactant, a pH regulator, an antiseptic, or an antioxidant as appropriate.

Examples of the ingredient to be used for formulation include, but not limited to, purified water, saline, phosphate buffer, pharmaceutically acceptable organic solvents such as dextrose, glycerol, and ethanol, animal or vegetable oils, lactose, mannitol, glucose, sorbitol, crystalline cellulose, hydroxypropyl cellulose, starch, corn starch, silicic anhydride, magnesium aluminum silicate, collagen, polyvinyl alcohol, polyvinyl pyrrolidine, carboxyvinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, tragacanth, casein, agar, polyethylene glycol, diglycerin, glycerin, propylene glycol, petrolatum, paraffin, octyl dodecyl myristate, isopropyl myristate, higher alcohol, stearyl alcohol, stearic acid, and human serum albumin.

Usable examples of the absorption promoter for improving absorption of a poorly absorbable drug having difficulty in transmucosal absorption of peptides include surfactants such as polyoxyethylene lauryl ethers, sodium lauryl sulfate, and saponin; bile salts such as glycolate, deoxycholate, and taurocholate; chelating agents such as EDTA and salicylic acids; fatty acids such as caproic acid, capric acid, lauric acid, oleic acid, linoleic acid, and mixed micelle; enamine derivatives, N-acylcollagen peptide, N-acylamino acid, cyclodextrins, chitosans, and nitric oxide donors.

Pills or tablets may also be sugar-, gastric-, or enteric-coated.

Injections may contain distilled water for injection, physiological saline, propylene glycol, polyethylene glycol, a vegetable oil, an alcohol, or the like. It may further contain a humectant, an emulsifier, a dispersant, a stabilizer, a dissolving agent, a solubilizing agent, an antiseptic, or the like.

The pharmaceutical composition of the present invention may be administered in combination with another drug or treatment method useful for the disease.

The dose of the pharmaceutical composition of the present invention when administered to mammals (for example, humans, mice, rats, guinea pigs, rabbits, dogs, horses, monkeys, pigs, and sheep), particularly, humans differs depending on the symptom, age, sex, weight and difference in sensitivity of patients, administration method, dosing interval, kind of the active ingredient, and kind of the formulation and is not particularly limited. For example, from 30 µg to 1000 mg, from 100 µg to 500 mg, or from 100 µg to 100 mg of the pharmaceutical composition may be administered once or in several portions. When it is administered by injection, from 1 µg/kg to 3000 µg/kg or from 3 µg/kg to 1000 µg/kg of it may be administered once or in several portions according to the weight of patients.

(Method for Producing a Peptide that Binds to a Target Substance and has High Stability)

The present invention also encompasses a method for enhancing a stability of a peptide that binds to a target substance.

As will be described later in Example, the c-Met protein-binding peptide of the present invention can be obtained by screening of a macrocyclic peptide library.

Peptides used as a drug are often regarded to have a problem in their stability in blood. There has therefore been an attempt to add various modifications to a constituent amino acid to provide a peptide having enhanced resistance to a protease or enhanced stability.

A peptide library however tends to be prepared in a translational synthesis system. By the above-described genetic code reprogramming, a certain amino acid modified can be introduced into a peptide to be translated and synthesized, but very complexed designing is necessary for adding modification to a plurality of amino acids.

Using the mRNA display method for screening through a peptide library enables simultaneous finding of the phenotype and genotype of a peptide to be bound to a target substance, but further analysis is required for finding whether the amino acid has been modified or not. In a peptide library, it is therefore difficult to verify what modification is effective even if an amino acid is modified.

The present inventors have conducted a study aimed at efficiently obtaining a peptide that binds to a target substance and at the same time has excellent stability. As a result, it has been found that this object can be achieved by, after N-methylation modification of at least one amino acid residue of a peptide selected by screening of a library and cyclization of the peptide, evaluating the stability of the peptide.

The "method for producing a peptide that binds to a target substance and at the same time, has high stability" according to the present invention therefore includes N-methylating or N-alkylating at least one amino acid residue of a peptide that binds to a target substance, cyclizing the peptide, and evaluating the stability of the peptide.

The "peptide that binds to a target substance" as described herein means a peptide which has already been recognized to bind to a target substance, and the degree of its affinity for the target substance is not limited insofar as it binds thereto. The peptide that binds to a target substance can be obtained, for example, by contacting a peptide library with the target substance, incubating the resulting library, and then selecting a peptide that binds to the target substance. The "method for producing a peptide that binds to a target substance and at the same time has high stability" according to the present invention is a method of carrying out screening using a peptide library and thereby selecting a peptide that binds to the target substance, and producing a highly stable peptide based on this peptide.

The "peptide that binds to a target substance" may be obtained by a method other than screening of a peptide library.

The step of "N-methylating or N-alkylating at least one amino acid residue of a peptide that binds to the target substance" described herein may be performed as appropriate by those skilled in the art. A peptide having at least one N-methylated or N-alkylated amino acid can be synthesized, for example, by synthesizing a peptide having an amino acid sequence same as that of the peptide that binds to a target substance by the above-described solid-phase synthesis method and using, during this synthesis, at least one N-methylated or N-alkylated amino acid. The peptide having N-methylated or N-alkylated amino acid means a peptide in which an N atom of the peptide bond has been methylated or alkylated. In the case of alkylation, the number of carbon atoms of the alkyl group may be set at 2, 3, 4, 5, 6, 7, 8, 9, 10, or the like.

The peptide having at least one N-methylated amino acid can also be prepared by translational synthesis applying the above-described genetic code reprogramming.

The number of amino acids to be N-methylated is not limited insofar as it is 1 or more and for example, it can be set at 2, 3, 4, 5, or the like.

The step of "cyclizing the peptide" described herein may also be performed as appropriate by those skilled in the art. A pair of the above-described "ring-forming amino acids" may be introduced into the terminal or non-terminal of the peptide having at least one N-methylated amino acid during synthesis of the peptide to enable the peptide thus synthesized to form a ring spontaneously.

Macrocyclic peptides can be found in the natural world and are known to have a stable conformation. Due to their size and complexity, macrocyclic peptides are known to show specificity higher than small non-cyclized peptides (White, T. R. et al., Nature chemical biology, 7(11), 810-7) and are expected to be an inhibitor against highly difficult targets such as molecules whose protein-protein interaction or low molecular compound binding site is unknown. Constraint by the cyclic structure is thought to improve the bioavailability of peptides or their resistance to metabolism.

Peptides obtained by carrying out the cyclizing step can have excellent specificity and binding affinity for a target substance and have high stability.

The step of "evaluating the stability of the peptide" described herein means a step of evaluating the stability of the peptide obtained by N-methylating at least one amino acid residue of the peptide that binds to a target substance and cyclizing the resulting peptide.

The "peptide having high stability" described herein means a peptide not easily degraded in a body fluid such as blood, in the serum, in a culture fluid, or in a buffer. It also encompasses, as well as a peptide having statistically significantly higher stability than that before N-methylation, a peptide having stability high enough to be recognized by those skilled in the art that it is high, though not statistically significantly high.

The step of evaluating the stability of the peptide can be carried out in a known manner as appropriate by those skilled in the art. For example, it can be evaluated by adding the peptide and a peptide serving as an internal standard to the serum and the like, incubating the resulting mixture at around 37° C., measuring the molecular weight by a liquid chromatograph mass spectrometer after a predetermined time, measuring a relative amount of the peptide to be evaluated to the internal standard peptide, and thereby determining the degraded amount.

This step may be performed not only in a sample derived from a living body but also by adding a specific peptidase to a buffer. By such methods, a peptide particularly excellent in resistance to a specific peptidase can be obtained.

In the "method for producing a peptide that binds to a target substance and at the same time has high stability" according to the present invention, the steps from the step of N-methylating an amino acid residue to the step of evaluating the stability of the peptide may be repeated to comprehensively study the influence of N-methylation on all the amino acids.

For example, the optimum peptide having enhanced stability while maintaining its affinity for the target substance can be found by successively performing N-methylation of the amino acid starting from the N-terminal amino acid, followed by the cyclization step and stability evaluation step.

In the "method for producing a peptide that binds to a target substance and at the same time has high stability" according to the present invention, the influence of N-methylation on only a specific amino acid may be studied instead of comprehensively studying it on all the amino chains.

As will be described later in Example, it has been found that a peptide obtained by N-methylating an arginine or lysine residue or an amino acid residue therearound tends to have high stability. There is therefore high possibility of efficiently producing a peptide that binds to a target substance and at the same time, has high stability by N-methylating an arginine residue or a lysine residue, or an amino acid therearound.

More specifically, the amino acid residue to be N-methylated may be an arginine residue, a lysine residue, or an amino acid residue within 2 amino acids from an arginine residue or a lysine residue; an arginine residue or a lysine residue that is in a region of two or more consecutive amino acids selected from the group consisting of arginine residues and lysine residues; or an amino acid residue within two amino acids from any of an arginine residue or a lysine residue that is in a region of two or more consecutive amino acids selected from the group consisting of arginine residues and lysine residues.

The term "amino acid residue within 2 amino acids from an arginine residue or a lysine residue" means that any amino acid residue of four amino acid residues including N-terminal side two amino acids and C-terminal side two amino acids, each from a certain arginine residue or lysine residue.

The term "an arginine residue or a lysine residue that is in a region of two or more consecutive amino acids selected from the group consisting of arginine residues and lysine residues" means at least one arginine or lysine in a region where two or more arginines, lysines, or arginine and lysine are continuous.

The term "an amino acid residue within two amino acids from any of an arginine residue or a lysine residue that is in a region where two or more consecutive amino acids selected from the group consisting of arginine residues and lysine residues" means any amino acid of four amino acid residues including N-terminal side two amino acids and C-terminal side two amino acids in a region where two or more arginines, lysines, or arginine and lysine are continuous.

The disclosure of the patent documents and non-patent documents cited herein is incorporated herein by reference in their entirety.

EXAMPLES

The present invention will hereinafter be described specifically based on Example. The present invention is not limited to or by them. Those skilled in the art can alter the present invention into various embodiments without departing from the meaning of the present invention and such an alteration is also encompassed within the scope of the present invention.

1. Construction of a Thioether Macrocyclic Peptide Library

For the peptide library to be used for the selection, the FIT system using an ARS ribozyme (flexizyme) and a reconstituted cell-free translation system (PURE System) was used.

By using an ARS ribozyme (eFx) and activated chloroacetyltyrosine (ClAc-L-Tyr-CME, ClAc-D-Tyr-CME), an initiator aminoacyl tRNA having ClAc-L-Tyr and ClAc-D-Tyr bound to the 3' end of an initiator tRNA was prepared.

In order to obtain a peptide library having a random sequence composed of from 4 to 15 amino acids sandwiched between ClAc-Tyr and cysteine (Cys) to be used for thioether cyclization, cDNAs having a sequence composed of an NNK codon repeated four to fifteen times were synthesized for the length of each of the random sequences.

An mRNA library was constructed by transcribing the cDNAs with T7 RNA polymerase to prepare mRNAs encoding a peptide and mixing mRNAs different in the length of the random sequence.

A puromycin linker was bound to the resulting mRNA library by using T4 RNA ligase.

In a cell-free translation system supplemented with 50 µM initiator aminoacyl tRNA synthesized on a methionine-deficient PURE system, 1.2 µM of the mRNA library was translated. The translation reaction was performed with 150 µL for $1^{st}$ round, 5 µL for $2^{nd}$ round, and 2.5 µL for $3^{rd}$ round and thereafter. After translation, the peptide was incubated at room temperature for 12 minutes to link, via puromycin, the peptide with an mRNA encoding it. Thioether bond formation and cyclization were promoted by adding 20 mM EDTA and incubating further at 37° C. for 30 minutes to obtain a thioether macrocyclic peptide library.

The thioether macrocyclic peptide-mRNA linked body was reverse transcribed with a reverse transcriptase (RTase) to synthesize a corresponding cDNA and a thioether macrocyclic peptide-mRNA-cDNA linked body was obtained.

REFERENCE DOCUMENTS

Y. Goto, T. Katoh, H. Suga, Nature Protocols, 6, 779-790 (2011)

Y. Hayashi, J. Morimoto, H. Suga, ACS Chemical Biology, 7, 607-613 (2012)

2. Selection of Thioether Macrocyclic Peptide that Binds to c-Met

Fc-bound magnetic beads obtained by binding Fc protein to Dynabeads Protein G were prepared. The thioether macrocyclic peptide library was added to the Fc-bound magnetic beads and the resulting mixture was incubated for 30 minutes (only $2^{nd}$ round and thereafter, twice at 4° C. and once at 37° C.) to remove the peptide binding to the Fc protein or Dynabeads Protein G.

Target beads to be used for selection were prepared by binding c-Met-Fc chimera protein to Dynabeads Protein G magnetic beads. The resulting c-Met bound beads and the thioether macrocyclic peptide treated as described above were incubated.

The beads were each washed three times with ice-cooled TBST and then incubated at 95° C. for 5 minutes in a PCR buffer to isolate a cDNA encoding the thioether macrocyclic peptide bound to each bead.

The cDNA thus isolated was quantitatively determined using real time PCR and a proportion of the c-Met binding thioether macrocyclic peptide in the library was calculated.

The cDNA was amplified by PCR and transcribed to prepare an mRNA library for the next round.

Upon improvement in the proportion of the c-Met binding thioether macrocyclic peptide in the library, the sequence of the cDNA was analyzed to identify the isolated thioether macrocyclic peptide sequence.

REFERENCE DOCUMENT

Y. Hayashi, J. Morimoto, H. Suga, ACS Chemical Biology, 7, 607-613 (2012)

The following are three examples of the macrocyclic peptides whose sequence has been identified (SEQ ID NOs: 4 to 6)

[Chemical formula 2]

$$\text{Ac-}^L\text{YISWNEFNSPNWRFITCG-NH}_2 \quad \text{(L5-2, S-bridge)}$$

$$\text{Ac-}^D\text{YRQFNRRTHEVWNLDCG-NH}_2 \quad \text{(D4-3, S-bridge)}$$

$$\text{Ac-}^D\text{YWYYAWDQTYKAFPCG-NH}_2 \quad \text{(D5-4, S-bridge)}$$

3. Chemical Synthesis of Thioether Macrocyclic Peptide

The isolated c-Met binding thioether macrocyclic peptide and C-terminal lysine-modified and cysteine-modified c-Met binding thioether macrocyclic peptides used for fluorescent labeling and dimer synthesis were synthesized using Fmoc solid phase synthesis. In the synthesis, common Fmoc solid-phase synthesis was performed manually or by an automated peptide synthesizer.

Condensation of an Fmoc amino acid was performed by adding, to a support, a mixture obtained by mixing the Fmoc amino acid, a condensation agent (mixture of HBTU and HOBt or COMU), and diisopropylethylamine (DIEA), each 5 times the equivalent with respect to the supported amount, in DMF and then reacting the resulting mixture for 30 minutes.

The Fmoc group was removed by reaction with 20% piperidine/80% DMF for 20 minutes.

The N terminal of the peptide was modified with a chloroacetyl group by reacting with 0.2 M NHS-chloroacetyl/DMF for one hour.

To the peptide thus synthesized, a trifluoroacetic acid (TFA)/ethanedithiol/triisopropylsilane/water (92.5:2.5:2.5:2.5) mixture was added. The resulting mixture was incubated at room temperature for 2 hours to cleave the peptide from the support and then, the side chain was deprotected.

The peptide thus cleaved was precipitated as a solid by adding diethyl ether in an amount of 10 times the liquid amount and then, dissolved in dimethylsulfoxide (DMSO) containing 0.1% TFA.

The peptide solution thus obtained was made basic by the addition of triethylamine (TEA). The resulting mixture was incubated at room temperature for one hour to cyclize the peptide thus synthesized.

The occurrence of the cyclization reaction was verified by MALDI-TOF-MS and the solution was made acidic again by the addition of TFA.

The cyclized peptide was purified by HPLC and its molecular weight was determined by MALDI-TOF-MS.

4. Fluorescein Modification of Thioether Macrocyclic Peptide

Fluorescein modified D5-4 peptide (D5-4-fluorescein) was prepared by modifying the synthesized peptide with fluorescein on a solid phase in the following manner.

First, the side chain Mmt protecting group of Lys at the C-terminal of D5-4 peptide was eliminated by incubating a support three times in a Dichloromethane/TFA/TIS (98:1:1) mixture for 15 minutes.

To the resulting support was added 3 times the equivalent of NHS-fluorescein dissolved in DMF with respect to the peptide and the resulting mixture was incubated at room temperature for 3 hours to bind fluorescein to the side chain of the C-terminal Lys.

The resulting peptide was cleaved as described above and purified to obtain D5-4-fluorescein.

Fluorescein-modified L5-2 peptide, D4-3 peptide, N-methylated D4-3 peptide, and c-Met-unbinding peptide (L5-2-fluorescein, D4-3-fluorescein, D4-3NMe-fluorescein, and D4-3scr-fluorescein, respectively) were prepared by obtaining L5-2, D4-3, D4-3NMe, and D4-3scr peptides having a lysine residue at the C terminal thereof by solid-phase synthesis, cleaving as described above, purifying by HPLC, and then modifying in a DMSO solution.

To the DMSO solution was added 1.5 times the equivalent of NHS-fluorescein with respect to the peptide dissolved in DMSO. Then, an adequate amount of TEA was added to make the solution basic, followed by reaction at 42° C. for one hour to add fluorescein to the side chain of the lysine.

TFA was added to make the reaction mixture acidic again and the resulting mixture was purified by HPLC to obtain L5-2-fluorescein and D4-3-fluorescein.

5. N-Methylation of Peptide

An N-methylated amino acid was introduced into the peptide by methylating an amino group of the corresponding amino acid on a support or using an Fmoc amino acid which had been N-methylated in advance.

Methylation on the support was performed in the following manner.

After condensation of the corresponding amino acid and elimination of Fmoc, the support was washed three times with N-methylpyrrolidone (NMP).

A solution was obtained by dissolving in NMP 4 times the equivalent of 2-nitrobenzenesulfonyl chloride (NBS-Cl) and 10 times the equivalent of 2,4,6-collidine, each with respect to the supporting amount. The resulting solution was added to the support and the resulting mixture was reacted at room temperature for 15 minutes to nitrobenzylate the amino group. The support was washed 5 times with NMP.

Three equivalents of 1,8-Diazabicyclo[5.4.0]undec-7-ene (DBU) were dissolved in NMP and the resulting solution was reacted with the support for 5 minutes. A solution obtained by dissolving 10 times the equivalent of dimethyl sulfate in NMP was added to the support and the resulting mixture was reacted at room temperature for 5 minutes. The above step was performed twice to methylate the amino group. The support was washed five times with NMP.

A solution obtained by dissolving 5 times the equivalent of DBU and 10 times the equivalent of 2-mercaptoethanol in NMP was added to the support, followed by reaction at room temperature for 5 minutes. The above step was performed twice to eliminate NBS and obtain a peptide in which an amino group of the corresponding amino acid had been methylated.

The followings are N-methylated peptides thus obtained.

[Chemical formula 3]

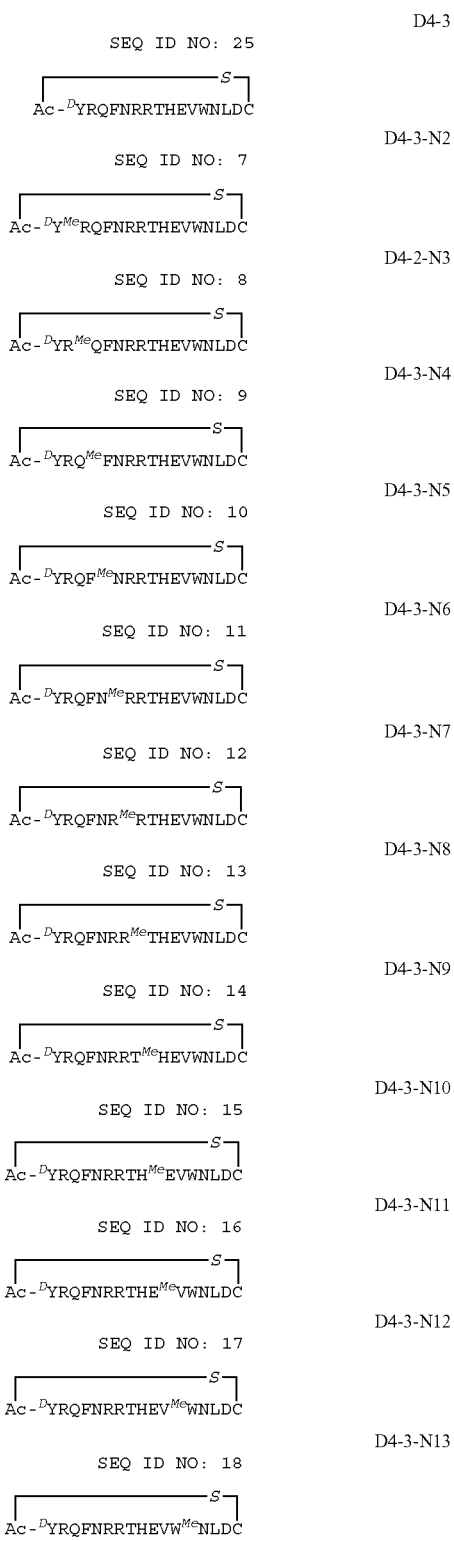

SEQ ID NO: 19    D4-3-N14

SEQ ID NO: 20    D4-3-N15

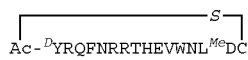

SEQ ID NO: 21    D4-3-N16

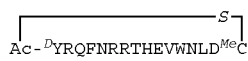

6. Dimerization of Thioether Macrocyclic Peptide

A thioether macrocyclic peptide having, at the C terminal thereof, Cys was chemically synthesized and purified by HPLC.

As a linker, BMH (Thermo Scientific), and Bis-MAL-PEG3 and Bis-MAL-PEG11 (Quanta Biodesign) having the following structures, respectively, were used.

A schematic view showing of dimerization of a macrocyclic peptide is shown in FIG. 1.

7. Verification of Localization of Fluorescein-Modified c-Met Binding Thioether Macrocyclic Peptide Using Cells To human c-Met expressing cells (human SNU-638 cells) or human c-Met non-expressing cells (human SNU-216 cells) cultured on a glass-bottom dish were added a RPMI1640 medium containing 1 mg/L of Hoechst 33342, a nuclear staining reagent, an anti-human c-Met antibody, and 1 uM of L5-2-fluorescein, D4-3-fluorescein, D5-4-fluorescein, D4-3NMe-fluorescein, or D4-3scr-fluorescein and the resulting mixture was incubated in 5% $CO_2$ at 37° C. for 5 minutes. Then, a RPMI1640 medium containing an HRP-anti-rat secondary antibody and 1 μM of L5-2-fluorescein, D4-3-fluorescein, D5-4-fluorescein, D4-3NMe-fluorescein, or D4-3scr-fluorescein was added and the resulting mixture was incubated in 5% $CO_2$ at 37° C. for 5 minutes.

The cells were washed three times with a D-MEM medium and were microscopically observed in a new RPMI1640 medium. The localization of the peptide was observed using a confocal fluorescence microscope for the microscopic observation.

[Chemical formula 4]

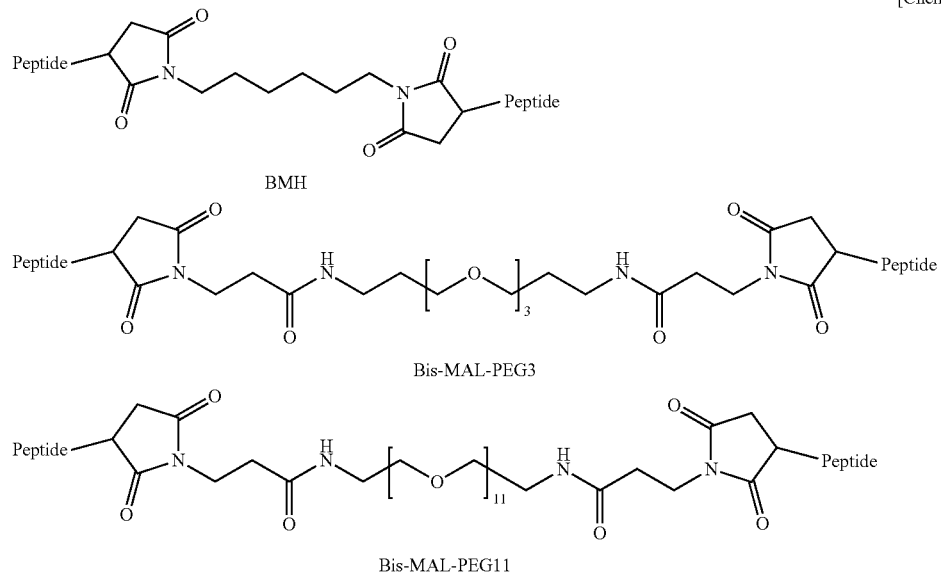

The dimerization reaction was performed by adding 11 mM of each of the peptides and 5 mM of each of the linkers to 50 mM Hepes-HCl (pH 7.5) and a 90% aqueous DMSO solution and then reacting the resulting mixture at 42° C. for 2 hours.

As exemplified below by L5-2 (SEQ ID NO: 22), the linker binds to the Cys residue at the C terminal.

[Chemical formula 5]

The reaction product was purified by HPLC and its molecular weight was determined by MALDI-TOF-MS.

Figure 2A:
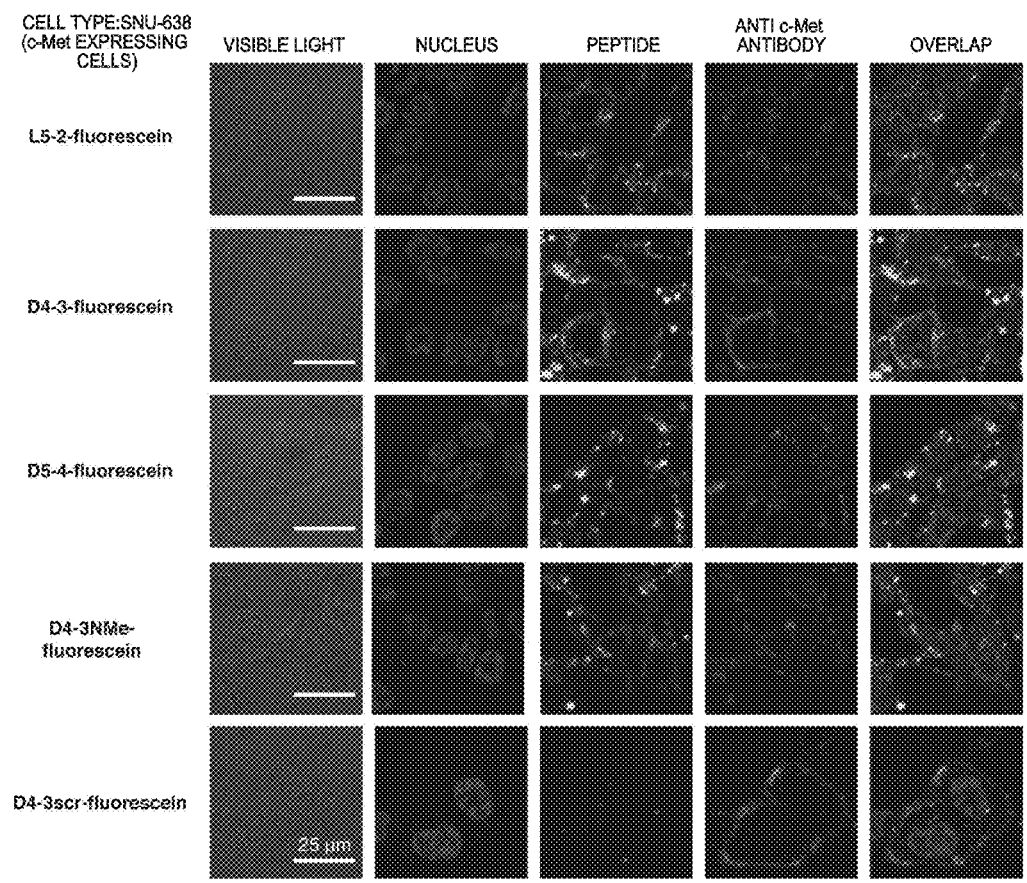
FIG. 2A shows the evaluation results of binding of peptides to c-Met expressing cells. The peptides used are L5-2-fluorescein, D5-4-fluorescein, D4-3-fluorescein, D4-3NMe-fluorescein, and D4-3scr-fluorescein obtained by fluorescently labeling c-Met protein-binding peptides (L5-2, D5-4, D4-3, and N-methylated D4-3) and a c-Met non-binding peptide.
Figure 2B:
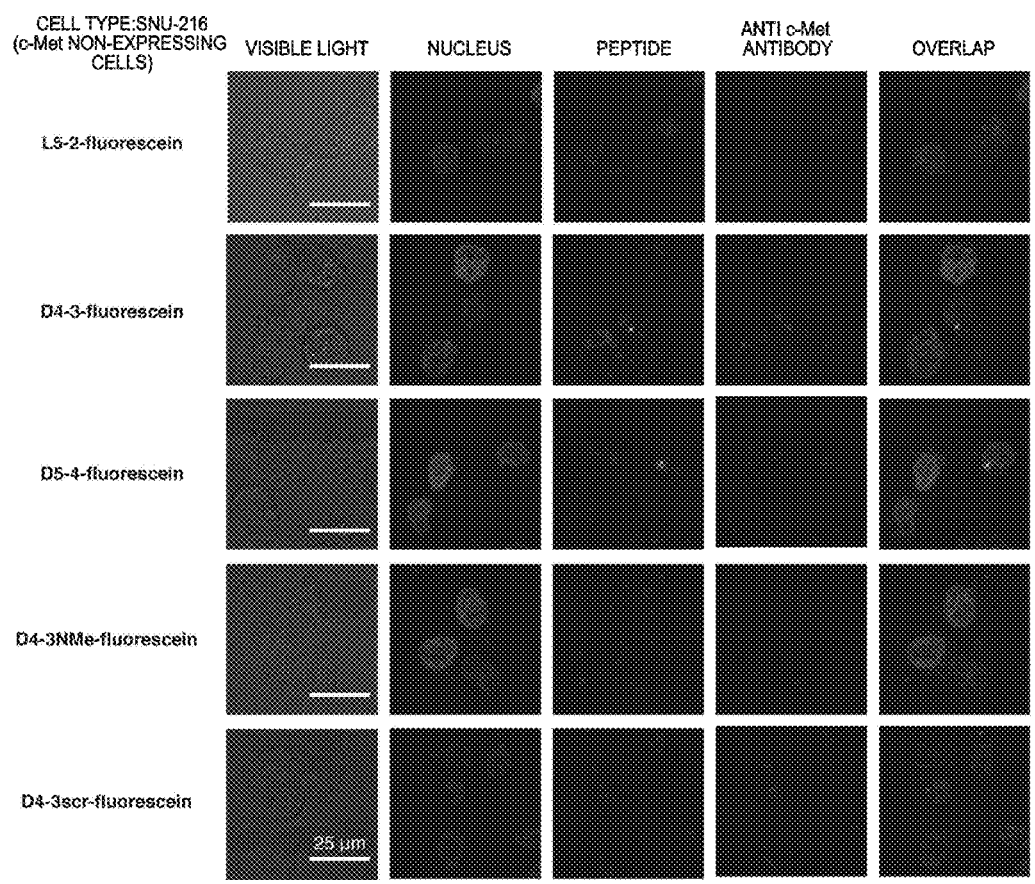
FIG. 2B shows the evaluation results of binding of peptides to c-Met non-expressing cells. The peptides used are L5-2-fluorescein, D5-4-fluorescein, D4-3-fluorescein, D4-3NMe-fluorescein, and D4-3scr-fluorescein obtained by fluorescently labeling c-Met protein-binding peptides (L5-2, D5-4, D4-3, N-methylated D4-3, and D4-3scr).

The results are shown in FIGS. 2A and B. It has been verified that L5-2-fluorescein, D4-3-fluorescein, D5-4-fluorescein, and D4-3NMe-fluorescein are colocalized with and bind to the c-Met expressing cells, while D4-3scr-fluorescein does not bind thereto. It has also been verified that these peptides do not bind to the c-Met non-expressing cells.

8. Evaluation of Stability of Thioether Macrocyclic Peptide in Serum

A DMSO solution of the thioether macrocyclic peptide to be evaluated was dissolved in a human serum pool to give a concentration of 1 μM. The human serum pool containing the thioether macrocyclic peptide thus prepared was incubated at 37° C.

After an elapse of the evaluation time, the human serum pool containing the thioether macrocyclic peptide was placed on ice and a peptide serving as an internal standard was added and mixed to give a concentration of 1 μM. The resulting mixture was added to a solid-phase extraction column (Hyper Sep SPE column, Thermo Scientific), washed with a 5% aqueous acetonitrile solution containing 0.1% TFA, and then purified by eluting with a 70% aqueous acetonitrile solution containing 0.1% TFA.

The molecular weight of the purified product was analyzed using LC-MS and the cleavage site in the serum was identified. In addition, the thioether macrocyclic peptide which had remained without being cleaved was quantitatively determined by comparing an amount relative to the internal standard at every incubation time.

The results are shown in the following table. As shown in the table, D4-3-N6, D4-3-N7, and D4-3-N8 obtained by N-methylating the periphery of a region of the D4-3 peptide where two arginines are continuous have drastically improved stability in serum, while they do not show marked deterioration in binding ability.

TABLE 8

| Peptide | $k_a$ ($10^5$ M$^{-1}$s$^{-1}$) | $k_d$ ($10^{-2}$ s$^{-1}$) | $K_D$ (nM) | Serum stability (1 h) |
|---|---|---|---|---|
| D4-3 | 13 | 1.1 | 8.5 | 3.7 |
| N2 | 7.1 | 1.0 | 14 | 5.4 |
| N3 | 0.27 | 0.31 | 120 | N.D. |
| N4 | 1.2 | 0.96 | 79 | 21.1 |
| N5 | 0.19 | 0.39 | 200 | N.D. |
| N6 | 1.2 | 0.41 | 34 | 85 |
| N7 | 0.53 | 6.9 | 130 | 92 |
| N8 | 0.27 | 0.60 | 220 | 81 |
| N9 | Not binding | | | N.D. |
| N10 | 0.25 | 0.75 | 300 | N.D. |
| N11 | 0.15 | 0.51 | 350 | N.D. |
| N12 | 0.55 | 0.86 | 160 | N.D. |
| N13 | 0.78 | 0.26 | 33 | 4.5 |
| N14 | 0.21 | 0.59 | 290 | N.D. |
| N15 | 3.0 | 4.6 | 160 | N.D. |
| N16 | 9.8 | 1.0 | 10 | 12 |

Figure 3:
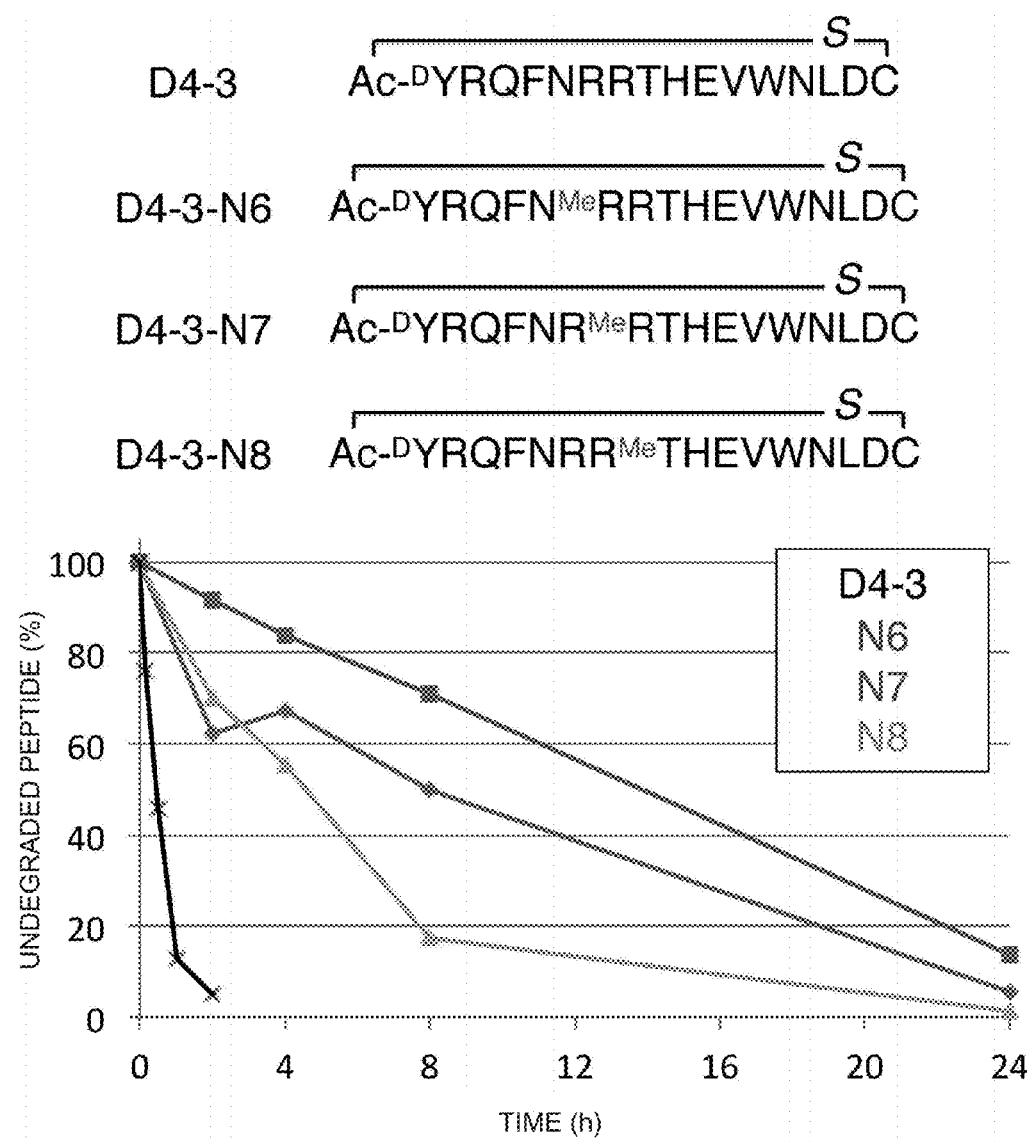
FIG. 3 shows the evaluation results of degradation of D4-3 peptide and N-methylated peptides thereof (D4-3-N6, D4-3-N7, and D4-3-N8) in the serum.

A time-dependent change in an undegraded proportion of the peptides D4-3, D4-3-N6, D4-3-N7, and D4-3-N8 is shown in FIG. 3.

Further, a peptide (D4-3NMe: SEQ ID NO: 23) was prepared by N-methylating two amino acids of D4-3. Measurement data of binding ability and stability in serum are shown in the following table.

TABLE 9

D4-3NMe

Ac-$^D$YRQFN$^{Me}$RRTHEVWNLD$^{Me}$CG-NH$_2$ (with S— bridge)

| Peptide | $k_a$ ($10^5$ M$^{-1}$s$^{-1}$) | $k_d$ ($10^{-2}$s$^{-1}$) | $K_D$ (nM) | Serum stability (4 h) |
|---|---|---|---|---|
| D4-3 | 13 | 1.1 | 8.5 | <3.7 |
| N6 | 1.2 | 0.41 | 34 | 67 |
| N16 | 9.8 | 1.0 | 10 | <12 |
| NMe (N6 + N16) | 3.9 | 0.21 | 5.2 | 63 |

9-1. Evaluation of Binding Ability of Thioether Macrocyclic Peptide by Surface Plasmon Resonance (SPR) Measurement Binding ability of the thioether macrocyclic peptide was evaluated by SPR measurement using Biacore (GE Healthcare).

As a sensor chip, Sensor Chip CM5 was used and an anti-IgG antibody was immobilized on a measurement lane and a control lane by using Human Antibody Capture Kit.

On the measurement lane was immobilized c-Met-Fc, while on the control lane was immobilized Fc protein.

As a running buffer, HBS-EP+ buffer containing 0.1% DMSO was used and a dissociation constant of the thioether macrocyclic peptide was calculated at 5 different concentrations by using the single-kinetics method.

The results are shown in the following table. It has been verified that D4-3NMe is considerably excellent in stability in serum and binding ability.

TABLE 10

| Peptide | Measurement of binding ability by surface plasmon resonance | | | Stability in human serum (undegraded portion/time) |
|---|---|---|---|---|
| | $k_a$ ($10^6$ M$^{-1}$s$^{-1}$) | $k_d$ ($10^{-2}$ s$^{-1}$) | $K_D$ (nM) | |
| L5-2 | 2.3 | 1.2 | 5.4 | 71%/2 h |
| D4-3 | 2.4 | 0.80 | 3.4 | 6%/2 h |
| D5-4 | 4.5 | 2.1 | 4.6 | 97%/2 h |
| D4-3NMe | 0.39 | 0.21 | 5.2 | 67%/4 h |
| D4-3scr | Not binding | | | Unmeasured |

As a peptide D4-3scr (SEQ ID NO: 24) for negative control, the following peptide was used.

[Chemical formula 6]

Ac-$^D$YERVNHLFRNQTWDRCG-NH$_2$ (with S— bridge)     D4-3scr 9-2. Evaluation of Binding Ability of Dimeric Peptide by Surface Plasmon Resonance (SPR) Measurement Results of evaluating the binding ability of each dimeric peptide by SPR as in 9-1 are shown in the following table. Any of the dimeric peptides exhibits high binding ability.

TABLE 11

| Peptide | Linker | $k_a$ ($10^6$ M$^{-1}$s$^{-1}$) | $k_d$ ($10^{-2}$ s$^{-1}$) | $K_D$ (nM) |
|---|---|---|---|---|
| L5-2 | Monomer | 2.3 | 1.2 | 5.4 |
| | BMH | 0.083 | 0.054 | 6.6 |
| | Bis-MAL-PEG3 | 0.22 | 0.042 | 1.9 |
| | Bis-MAL-PEG11 | 0.098 | 0.031 | 3.1 |
| D4-3 | Monomer | 2.4 | 0.80 | 3.4 |
| | BMH | 2.0 | 0.091 | 0.45 |
| | Bis-MAL-PEG3 | 1.1 | 0.070 | 0.64 |
| | Bis-MAL-PEG11 | 1.2 | 0.11 | 0.90 |
| D5-4 | Monomer | 4.5 | 2.1 | 4.6 |
| | BMH | 0.046 | 0.055 | 12 |
| | Bis-MAL-PEG3 | 0.12 | 0.054 | 4.7 |
| | Bis-MAL-PEG11 | 5.3 | 1.1 | 2.1 |
| D4-3NMe | Monomer | 0.39 | 0.21 | 5.2 |
| | Bis-MAL-PEG11 | 0.49 | 0.040 | 0.81 |
| D4-3scr | Monomer | Not binding | | |
| | BMH | Not binding | | |

10. Evaluation of Activity of Dimeric Peptide by Phospho-RTK Array

The optimum concentration of each dimeric peptide was added to cultured EHMES-1 cells derived from human mesothelioma and the resulting mixture was incubated for 10 minutes to stimulate the cells. As a control experiment, 2 nM recombinant human HGF protein was added, followed by incubation for 10 minutes.

The resulting cells were lyzed and the lysate thus obtained was analyzed using Phospho-RTK array (R&D Systems) to evaluate whether or not the c-Met of the cells was phosphorylated.

Figure 4:
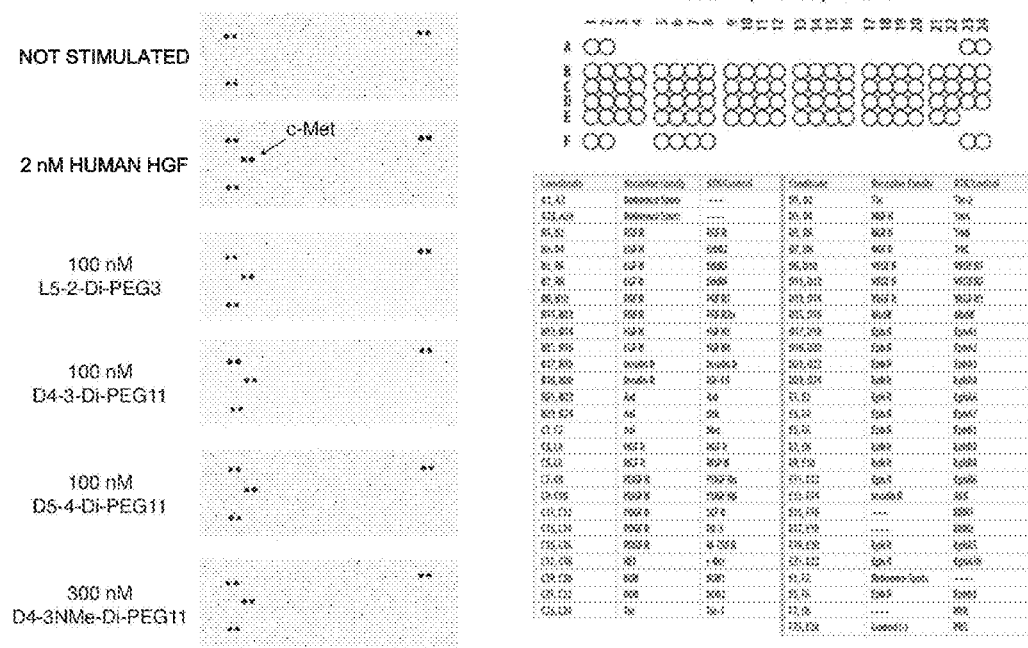
FIG. 4 shows the results of evaluating autophosphorylation of c-Met proteins induced by c-Met binding dimeric peptides (peptide complexes according to the present invention). Evaluation was made by adding each dimeric peptide at an optimum concentration to cultured EHMES-1 cells derived from human mesothelioma to stimulate them and analyzing the cell lysate by Phospho-RTK array (R&D Systems).

The results are shown in FIG. 4. As shown in the drawing, it has been verified that autophosphorylation is induced by the addition of each of dimerized L5-2, D4-3, D5-4, and N-methylated D4-3 peptides in a manner similar to the addition of HGF. In addition, it has been demonstrated that since another RTK (receptor tyrosine kinase) is not phosphorylated, these dimeric peptides have high selectivity to c-Met.

11. Evaluation of Activity of Dimeric Peptide by Western Blotting

The optimum concentration of each of the dimeric peptides was added to cultured EHMES-1 cells derived from human mesothelioma and the resulting mixture was incubated for 10 minutes to stimulate the cells. As a control experiment, 2 nM of a recombinant human HGF protein was added, followed by incubation for 10 minutes.

Figure 5:
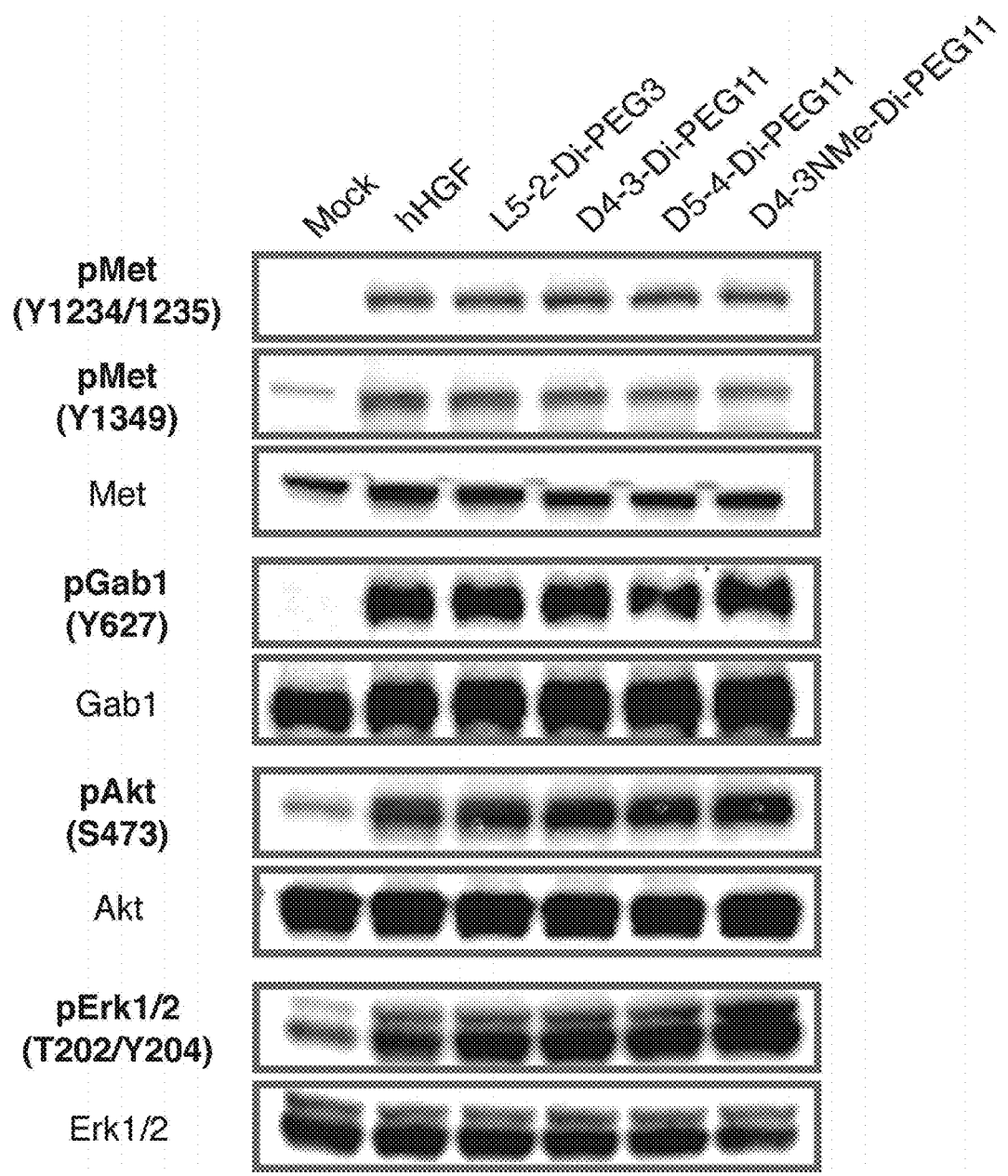
FIG. 5 shows the results of verifying autophosphorylation of c-Met proteins and phosphorylation of Gab1, Akt, and Erk1/2 (MAPK) proteins in downstream of a signaling pathway, each induced by c-Met binding dimeric peptides (peptide complexes according to the present invention). The evaluation was conducted by western blotting using antibodies against respective phosphorylated proteins.

The cells were lysed and the resulting lysate was electrophoresed using a 10% modified polyacrylamide gel. After transcription of the protein thus separated to an Immobilon-P PVDF membrane (Millipore) and blocking with PVDF Blocking Reagent for Can Get Signal (TOYOBO), a primary antibody reaction of it was performed overnight at 4° C. in Can Get Signal Solution 1 (TOYOBO). As the antibody, anti-Met (Millipore, EP1454Y), anti-Phospho-Met Tyr1234/1235 (Cell Signaling Technology, D26), anti-Phospho-Met Tyr1349 (Millipore, 07-808), anti-Akt (Cell Signaling Technology, 11E7), anti-Phospho-Akt Thr308 (Cell Signaling Technology, D25E6), anti-Erk1/2 (Cell Signaling Technology, 137F5), anti-Phospho-Erk1/2 Thr202/Tyr204 (Cell Signaling Technology, D13.14.4E), anti-Gab1 (Cell Signaling Technology), or anti-Phospho-Gab1 Tyr 627 (Cell Signaling Technology, C32H2) was used. Then, a secondary antibody reaction was performed at room temperature for one hour in Can Get Signal Solution 2 (TOYOBO) by using an anti-rabbit antibody HRP conjugate. Luminata Forte HRP substrate (Millipore), that is, an HRP substrate, was added to the membrane and the resulting mixture was reacted for one minute. Chemiluminescence was observed using ImageQuant LAS 350. The results are shown in FIG. 5. It has been demonstrated that all the dimeric peptides, similar to HGF, promote phosphorylation of each of c-Met, Gab1, Akt, and Erk proteins. These proteins are adaptor proteins important in c-Met signaling pathway. The results have demonstrated that the dimeric peptides activate a c-Met pathway in the same manner as stimulation by HGF which is a natural ligand.

12. Evaluation of Activity of Dimeric Peptide by ELISA

Each dimeric peptide was added to human EHMES-1 cells and the mixture was incubated for 10 minutes to stimulate the cells.

As a control experiment, a recombinant human HGF protein was added and the mixture was incubated for 10 minutes to stimulate cells.

A phosphorylation level of c-Met was quantitatively analyzed using ELISA.

The results are shown in Table 12. The dimerized L5-2, D4-3, D5-4, and N-methylated D4-3 peptides induce autophosphorylation of c-Met. The autophosphorylation degree differs, depending on the kind of the linker and the linker that has increased the autophosphorylation level differs, depending on the kind of the peptides.

TABLE 12

| Peptide | Linker | Activity |
| --- | --- | --- |
| L5-2 | BMH | Low |
|  | Bis-MAL-PEG3 | High |
|  | Bis-MAL-PEG11 | Low |
| D4-3 | BMH | Low |
|  | Bis-MAL-PEG3 | Low |
|  | Bis-MAL-PEG11 | High |
| D5-4 | BMH | High |
|  | Bis-MAL-PEG3 | High |
|  | Bis-MAL-PEG11 | High |
| D4-3NMe | Bis-MAL-PEG11 | High |
| D4-3scr | BMH | No |

13. Evaluation of Cell Growth and Cell Migration Activities of Dimeric Peptides

Dimeric peptides were added to human Hcc-827 cells whose cell growth was inhibited by the addition of Iressa and the resulting mixture was cultured to activate the cell growth ability via a c-Met signaling pathway. The cell count of the thus-cultured cells was quantitatively determined by the assay using MTS (3-(4,5-dimethylthiazol-2-yl)-5-(3carboxymethoxyphenyl)-2-(4-sulphophenyl)-2H-tetrazolium, inner salt).

In addition, human HuCCT1 cells were seeded on a pore-containing plate and cultured in a medium mixed with each of the dimeric peptides to evaluate activation of cell migration ability.

The results are shown in Table 13. The dimerized L5-2, D4-3, D5-4, and N-methylated D4-3 peptides activate cell growth and cell migration.

TABLE 13

| Peptide | Linker | c-Met phosphorylation | Cell growth | Cell migration |
| --- | --- | --- | --- | --- |
| L5-2 | Monomer | Not promote | Not activate | N.D. |
|  | BMH | Promote | Activate | N.D. |
|  | Bis-MAL-PEG3 | Promote | N.D. | N.D. |
|  | Bis-MAL-PEG11 | Promote | N.D. | Activate |
| D4-3 | Monomer | Not promote | Not activate | N.D. |
|  | BMH | Promote | Activate | N.D. |
|  | Bis-MAL-PEG3 | Promote | N.D. | N.D. |
|  | Bis-MAL-PEG11 | Promote | N.D. | Activate |
| D5-4 | Monomer | Not promote | Not activate | N.D. |
|  | BMH | Promote | Activate | N.D. |
|  | Bis-MAL-PEG3 | Promote | N.D. | N.D. |
|  | Bis-MAL-PEG11 | Promote | N.D. | Activate |
| D4-3NMe | Monomer | Not promote | N.D. | N.D. |
|  | Bis-MAL-PEG11 | Promote | N.D. | Activate |
| D4-3scr | Monomer | Not promote | N.D. | N.D. |
|  | BMH | Not promote | N.D. | Not activate |

N.D.: Not determined

What is claimed is:

1. A peptide complex comprising two or more peptides that bind to c-mesenchymalepithelial transition (c-Met) proteins and a linker that links the two or more peptides to one another, wherein the linker is selected from the group consisting of bismaleimidohexane (BMH), Bis-[1,13-(3-maleimidopropionyl)amido]-4,7,10-trioxatridecane (Bis-MAL-PEG3), and Bis-[1,35-(3-maleimidopropionyl)amido]-3,6,9,12,15,18,21,24,27,30,33-undecaoxapentatricontane (Bis-MAL-PEG11).

2. The peptide complex according to claim 1, wherein each of the two or more peptides that bind to c-Met proteins is macrocyclized.

3. The peptide complex according to claim 1, wherein the two or more peptides that bind to c-Met proteins are each independently selected from the group consisting of the following (i) to (vi):

(i)
ISWNEFNSPNWRFIT;   (SEQ ID NO: 1)

(ii)
RQFNRRTHEVWNLD;   (SEQ ID NO: 2)

(iii)
WYYAWDQTYKAFP;   (SEQ ID NO: 3)

(iv) a peptide that has any of the amino acid sequences (i) to (iii) in which one or two amino acids have been substituted and binds to a c-Met protein;
(v) a peptide that has 90% or more sequence identity with any of the amino acid sequences (i) to (iii) and binds to a c-Met protein; and
(vi) a peptide of any one of (i) to (v) in which at least one amino acid has been modified by phosphorylation, methylation, acetylation, adenylation, ADP ribosylation, or glycosylation.

4. The peptide complex according to claim 3, wherein the two or more peptides that bind to c-Met proteins have, at the terminal or non-terminal thereof, an amino acid residue for macrocyclizing the peptides.

5. A c-Met protein agonist comprising the peptide complex according to claim 1.

6. A pharmaceutical composition comprising the peptide complex according to claim 1.

7. A protecting agent or regeneration promoting agent of an organ after organ transplantation, comprising the peptide complex according to claim 1.

8. The peptide complex according to claim 1, wherein at least one amino acid in at least one peptide of two or more peptides that bind to c-Met proteins is N-methylated or N-alkylated.

9. A method for treating a disease selected from the group consisting of acute hepatitis, fulminant hepatitis, cirrhosis, biliary atresia, fatty liver, acute renal insufficiency, chronic renal insufficiency, diabetic nephropathy, acute pneumonia, pulmonary fibrosis, angiopathy, myocardial infarction, dilated cardiomyopathy, skin ulcer, cerebral infarction, and amyotrophic lateral sclerosis in a subject in need thereof comprising administering to the subject the peptide complex according to claim 1.

* * * * *

SEQUENCE LISTING

<160> NUMBER OF SEQ ID NOS: 25

<210> SEQ ID NO 1
<211> LENGTH: 15
<212> TYPE: PRT
<213> ORGANISM: Artificial Sequence

```
<220> FEATURE:
<223> OTHER INFORMATION: c-Met protein binding peptide.

<400> SEQUENCE: 1

Ile Ser Trp Asn Glu Phe Asn Ser Pro Asn Trp Arg Phe Ile Thr
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: c-Met protein binding peptide.

<400> SEQUENCE: 2

Arg Gln Phe Asn Arg Arg Thr His Glu Val Trp Asn Leu Asp
1               5                   10

<210> SEQ ID NO 3
<211> LENGTH: 13
<212> TYPE: PRT
<213> ORGANISM: Artificial Sequence
<220> FEATURE:
<223> OTHER INFORMATION: c-Met protein binding peptide.

<400> SEQUENCE: 3

Trp Tyr Tyr Ala Trp Asp Gln Thr Tyr Lys Ala Phe Pro
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Macrocyclic peptide L5-2.
<220> FEATURE:
<221> NAME/KEY: DISULFID
<222> LOCATION: (1)..(17)
<223> OTHER INFORMATION: Disulfide bridge between amino acid residues 1
      and 17.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: L-Tyrosine.
<220> FEATURE:
<221> NAME/KEY: MOD_RES
<222> LOCATION: (18)..(18)
<223> OTHER INFORMATION: AMIDATION

<400> SEQUENCE: 4

Tyr Ile Ser Trp Asn Glu Phe Asn Ser Pro Asn Trp Arg Phe Ile Thr
1               5                   10                  15

Cys Gly

<210> SEQ ID NO 5
<211> LENGTH: 17
<212> TYPE: PRT
<213> ORGANISM: Artificial Sequence
<220> FEATURE:
<223> OTHER INFORMATION: Macrocyclic peptide D4-3.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (17)..(17)
<223> OTHER INFORMATION: AMIDATION

<400> SEQUENCE: 5

Tyr Arg Gln Phe Asn Arg Arg Thr His Glu Val Trp Asn Leu Asp Cys
 1               5                  10                  15

Gly

<210> SEQ ID NO 6
<211> LENGTH: 16
<212> TYPE: PRT
<213> ORGANISM: Artificial Sequence
<220> FEATURE:
<223> OTHER INFORMATION: Macrocyclic peptide D5-4.
<220> FEATURE:
<221> NAME/KEY: DISULFID
<222> LOCATION: (1)..(15)
<223> OTHER INFORMATION: Disulfide bridge between amino acid residues 1
      and 15.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (16)..(16)
<223> OTHER INFORMATION: AMIDATION

<400> SEQUENCE: 6

Tyr Trp Tyr Tyr Ala Trp Asp Gln Thr Tyr Lys Ala Phe Pro Cys Gly
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Macrocyclic peptide D4-3-N2.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 7
```

Tyr Arg Gln Phe Asn Arg Arg Thr His Glu Val Trp Asn Leu Asp Cys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Macrocyclic peptide D4-3-N3.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 8

Tyr Arg Gln Phe Asn Arg Arg Thr His Glu Val Trp Asn Leu Asp Cys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Macrocyclic peptide D4-3-N4.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 9

Tyr Arg Gln Phe Asn Arg Arg Thr His Glu Val Trp Asn Leu Asp Cys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Macrocyclic peptide D4-3-N5.

```
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 10

Tyr Arg Gln Phe Asn Arg Arg Thr His Glu Val Trp Asn Leu Asp Cys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Macrocyclic peptide D4-3-N6.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (6)..(6)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 11

Tyr Arg Gln Phe Asn Arg Arg Thr His Glu Val Trp Asn Leu Asp Cys
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Macrocyclic peptide D4-3-N7.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
```

```
<222> LOCATION: (1)..(1)
<223> OTHER INFORMATION: D-Tyrosine.
<220> FEATURE:
<221> NAME/KEY: MOD_RES
<222> LOCATION: (7)..(7)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 12

Tyr Arg Gln Phe Asn Arg Arg Thr His Glu Val Trp Asn Leu Asp Cys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Macrocyclic peptide D4-3-N8.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 13

Tyr Arg Gln Phe Asn Arg Arg Thr His Glu Val Trp Asn Leu Asp Cys
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Macrocyclic peptide D4-3-N9.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (16)..(16)
<223> OTHER INFORMATION: AMIDATION
```

-continued

```
<400> SEQUENCE: 14

Tyr Arg Gln Phe Asn Arg Arg Thr His Glu Val Trp Asn Leu Asp Cys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Macrocyclic peptide D4-3-N10.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (10)..(10)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 15

Tyr Arg Gln Phe Asn Arg Arg Thr His Glu Val Trp Asn Leu Asp Cys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Macrocyclic peptide D4-3-N11.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (11)..(11)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 16

Tyr Arg Gln Phe Asn Arg Arg Thr His Glu Val Trp Asn Leu Asp Cys
1               5                   10                  15

<210> SEQ ID NO 17
<211> LENGTH: 16
<212> TYPE: PRT
<213> ORGANISM: Artificial Sequence
<220> FEATURE:
```

<223> OTHER INFORMATION: Macrocyclic peptide D4-3-N12.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (12)..(12)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 17

Tyr Arg Gln Phe Asn Arg Arg Thr His Glu Val Trp Asn Leu Asp Cys
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Macrocyclic peptide D4-3-N13.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 18

Tyr Arg Gln Phe Asn Arg Arg Thr His Glu Val Trp Asn Leu Asp Cys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Macrocyclic peptide D4-3-N14.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:

```
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 19

Tyr Arg Gln Phe Asn Arg Arg Thr His Glu Val Trp Asn Leu Asp Cys
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Macrocyclic peptide D4-3-N15.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (15)..(15)
<223> OTHER INFORMATION: METHYLATION
<220> FEATURE:
<221> NAME/KEY: MOD_RES
<222> LOCATION: (16)..(16)
<223> OTHER INFORMATION: AMIDATION

<400> SEQUENCE: 20

Tyr Arg Gln Phe Asn Arg Arg Thr His Glu Val Trp Asn Leu Asp Cys
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Macrocyclic peptide D4-3-N16.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (16)..(16)
<223> OTHER INFORMATION: METHYLATION
<220> FEATURE:
<221> NAME/KEY: MOD_RES
<222> LOCATION: (16)..(16)
<223> OTHER INFORMATION: AMIDATION
```

<400> SEQUENCE: 21

Tyr Arg Gln Phe Asn Arg Arg Thr His Glu Val Trp Asn Leu Asp Cys
1               5                   10                  15

<210> SEQ ID NO 22
<211> LENGTH: 20
<212> TYPE: PRT
<213> ORGANISM: Artificial Sequence
<220> FEATURE:
<223> OTHER INFORMATION: Macrocyclic peptide L5-2.
<220> FEATURE:
<221> NAME/KEY: DISULFID
<222> LOCATION: (1)..(17)
<223> OTHER INFORMATION: Disulphide bridge between amino acid residue 1
      and 17.
<220> FEATURE:
<221> NAME/KEY: MISC_FEATURE
<222> LOCATION: (1)..(1)
<223> OTHER INFORMATION: L-Tyrosine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (19)..(19)
<223> OTHER INFORMATION: bAla.
<220> FEATURE:
<221> NAME/KEY: MISC_FEATURE
<222> LOCATION: (20)..(20)
<223> OTHER INFORMATION: Cysteine to which a Linker binds.
<220> FEATURE:
<221> NAME/KEY: MOD_RES
<222> LOCATION: (20)..(20)
<223> OTHER INFORMATION: AMIDATION

<400> SEQUENCE: 22

Tyr Ile Ser Trp Asn Glu Phe Asn Ser Pro Asn Trp Arg Phe Ile Thr
1               5                   10                  15

Cys Gly Xaa Cys
            20

<210> SEQ ID NO 23
<211> LENGTH: 17
<212> TYPE: PRT
<213> ORGANISM: Artificial Sequence
<220> FEATURE:
<223> OTHER INFORMATION: Macrocyclic peptide D4-3 NMe.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MISC_FEATURE
<222> LOCATION: (1)..(1)
<223> OTHER INFORMATION: D-Tyrosine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: METHYLATION
<220> FEATURE:
<221> NAME/KEY: MOD_RES
<222> LOCATION: (16)..(16)
<223> OTHER INFORMATION: METHYLATION
<220> FEATURE:
<221> NAME/KEY: MOD_RES
<222> LOCATION: (17)..(17)
<223> OTHER INFORMATION: AMIDATION

```
<400> SEQUENCE: 23

Tyr Arg Gln Phe Asn Arg Arg Thr His Glu Val Trp Asn Leu Asp Cys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Macrocyclic peptide D4-3scr.
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MISC_FEATURE
<222> LOCATION: (1)..(1)
<223> OTHER INFORMATION: D-Tyrosine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (17)..(17)
<223> OTHER INFORMATION: AMIDATION

<400> SEQUENCE: 24

Tyr Glu Arg Val Asn His Leu Phe Arg Asn Gln Thr Trp Asp Arg Cys
1               5                   10                  15

Gly

<210> SEQ ID NO 25
<211> LENGTH: 16
<212> TYPE: PRT
<213> ORGANISM: Artificial Sequence
<220> FEATURE:
<223> OTHER INFORMATION: Macrocyclic peptide
<220> FEATURE:
<221> NAME/KEY: DISULFID
<222> LOCATION: (1)..(16)
<223> OTHER INFORMATION: Disulfide bridge between amino acid residues 1
      and 16.
<220> FEATURE:
<221> NAME/KEY: MISC_FEATURE
<222> LOCATION: (1)..(1)
<223> OTHER INFORMATION: D-Tyrosine.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 25

Tyr Arg Gln Phe Asn Arg Arg Thr His Glu Val Trp Asn Leu Asp Cys
1               5                   10                  15
```